(12) United States Patent
Kang et al.

(10) Patent No.: US 11,472,825 B2
(45) Date of Patent: Oct. 18, 2022

(54) REAL-TIME FLUORESCENCE IMAGING SENSOR FOR MEASURING GLUTATHIONE IN ORGANELLE AND PREPARATION METHOD THEREFOR

(71) Applicant: CELL2IN, INC., Seoul (KR)

(72) Inventors: Heun Soo Kang, Seoul (KR); Hye Mi Kim, Seoul (KR); Ji Eun Song, Seoul (KR); Myoung Jin Kim, Seoul (KR); Ki Hang Choi, Seoul (KR)

(73) Assignee: CELL2IN, INC., Seoul (KR)

( * ) Notice: Subject to any disclaimer, the term of this patent is extended or adjusted under 35 U.S.C. 154(b) by 370 days.

(21) Appl. No.: 16/640,717

(22) PCT Filed: Aug. 23, 2018

(86) PCT No.: PCT/KR2018/009743
§ 371 (c)(1),
(2) Date: Feb. 20, 2020

(87) PCT Pub. No.: WO2019/039888
PCT Pub. Date: Feb. 28, 2019

(65) Prior Publication Data
US 2020/0354388 A1 Nov. 12, 2020

(30) Foreign Application Priority Data
Aug. 24, 2017 (KR) ........................ 10-2017-0107429

(51) Int. Cl.
| | |
|---|---|
| *C07F 9/6561* | (2006.01) |
| *C07D 491/147* | (2006.01) |
| *G01N 21/64* | (2006.01) |
| *G01N 33/483* | (2006.01) |
| *G01N 33/52* | (2006.01) |

(52) U.S. Cl.
CPC ........ *C07F 9/6561* (2013.01); *C07D 491/147* (2013.01); *G01N 21/64* (2013.01); *G01N 33/483* (2013.01); *G01N 33/52* (2013.01)

(58) Field of Classification Search
CPC ...... G01N 21/64; G01N 33/483; G01N 33/52; C07D 491/47; C07F 9/6561
USPC ........................................................ 424/9.6
See application file for complete search history.

(56) References Cited

U.S. PATENT DOCUMENTS

| | | |
|---|---|---|
| 2004/0191913 A1 | 9/2004 | Yoshikawa |
| 2017/0007723 A1 | 1/2017 | Duvall et al. |
| 2019/0204331 A1 | 7/2019 | Ki et al. |

FOREIGN PATENT DOCUMENTS

| | | |
|---|---|---|
| CN | 103820104 A | 5/2014 |
| KR | 10-1575846 B1 | 12/2015 |
| KR | 10-2016-0059978 A | 5/2016 |

OTHER PUBLICATIONS

Chemical Abstracts Registry No. 374544-06-6, STN Express, Entered STN Dec. 7, 2001.
Hongyan Liu et al., "Anti-oxidant pathways are stimulated by mesenchymal stromal cells in renal repair after ischemic injury", Cytotherapy, 14, 162-172 (2012).
International Search Report dated Nov. 16, 2018 for International Application No. PCT/KR2018/009743, 4 pages.
Written Opinion dated Nov. 16, 2018 for International Application No. PCT/KR2018/009743, 11 pages, including Machine Translation.
Project Report HI10C0185—Heath Technology R&D Project—Converging translational research center for the development of pulmonary fibrosis therapeutics—Project Period May 1, 2010-Mar. 31, 2014. English Language summary at p. 5.
CAS Registry Entry 374544-86-5. Entered STN Dec. 7, 2001.
A Young Cho and Kihang Choi, "A Coumarin-based Fluorescence Sensor for the Reversible Detection of Thiols," Chem. Lett., 41, 1611012 (2012).

*Primary Examiner* — Kahsay Habte
(74) *Attorney, Agent, or Firm* — McDonnell Boehnen Hulbert & Berghoff LLP

(57) ABSTRACT

The present invention relates to a real-time fluorescence imaging sensor for measuring glutathione in cell organelles and a method for fabricating the same. More specifically, the present invention relates to a novel compound for measuring glutathione in cell organelles, a method for preparing the novel compound, a real-time fluorescence imaging sensor for measuring glutathione in cell organelles, which comprises the novel compound, a method for fabricating the imaging sensor, and a method of measuring glutathione in cell organelles by use of the imaging sensor.
When the composition comprising the compound according to the present invention is used, it can measure the antioxidant activity of the organelle mitochondria or Golgi apparatus in living cells, particularly stem cells, and can screen highly active stem cells based on the results obtained by measuring the antioxidant activity of the cell organelle.

15 Claims, 9 Drawing Sheets

[FIG. 1]
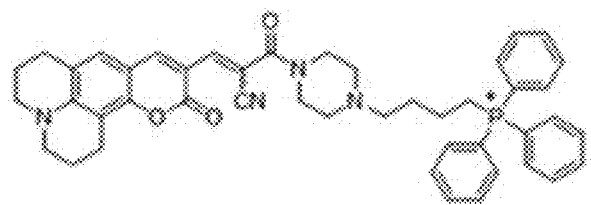
[FIG. 2A]
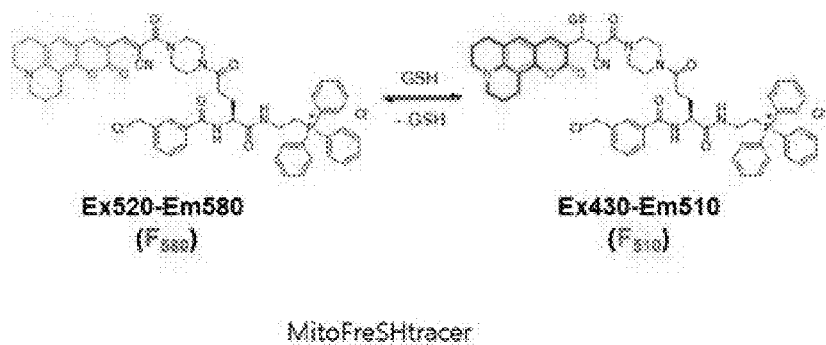
MitoFreSHtracer

[FIG. 2B]
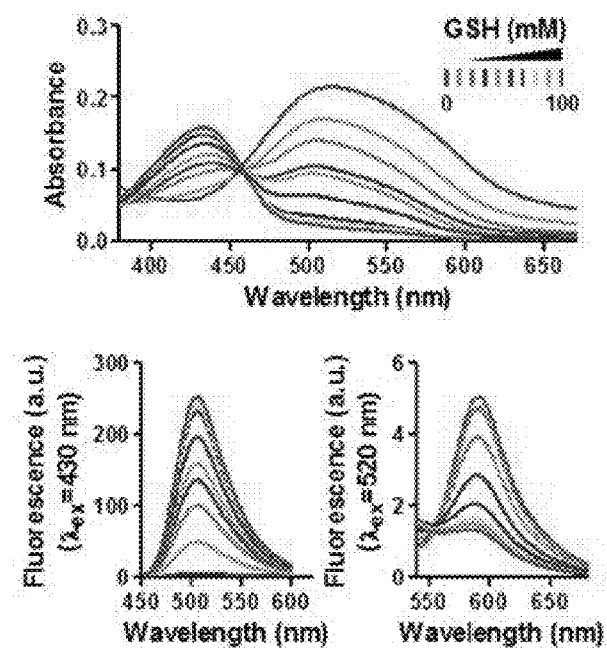
[FIG. 2C]
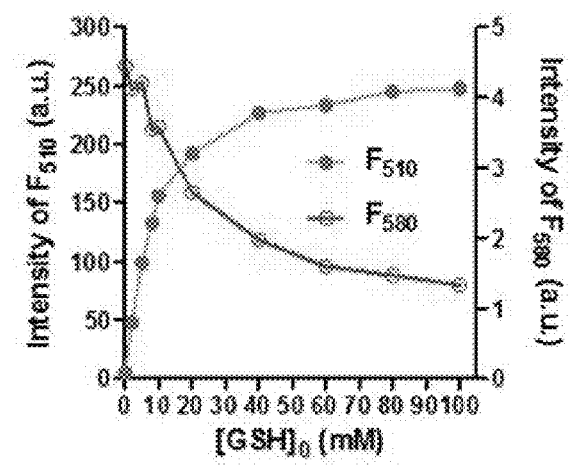

[FIG. 2D]
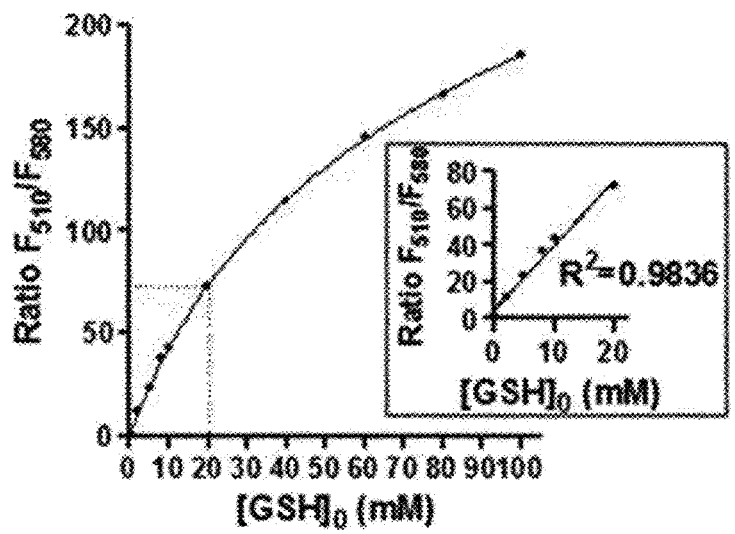
[FIG. 3]
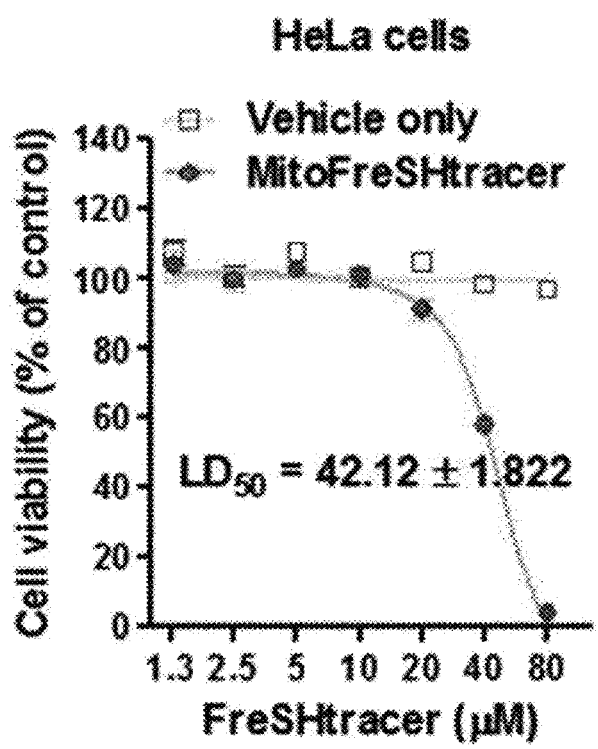

[FIG. 4A]
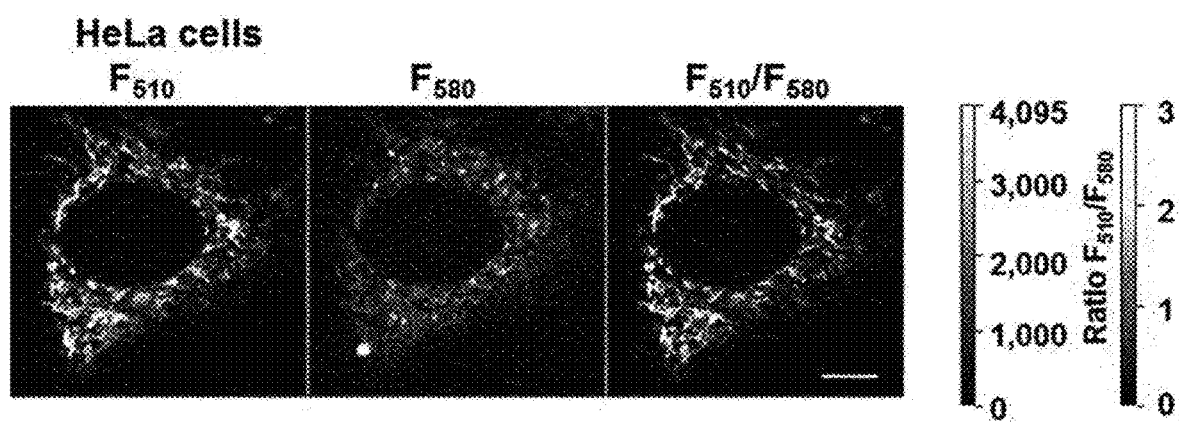
[FIG. 4B]
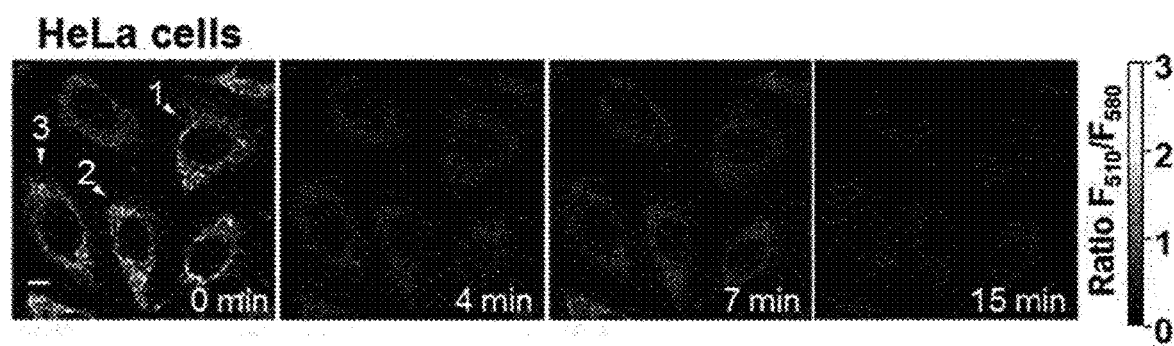

[FIG. 4C]
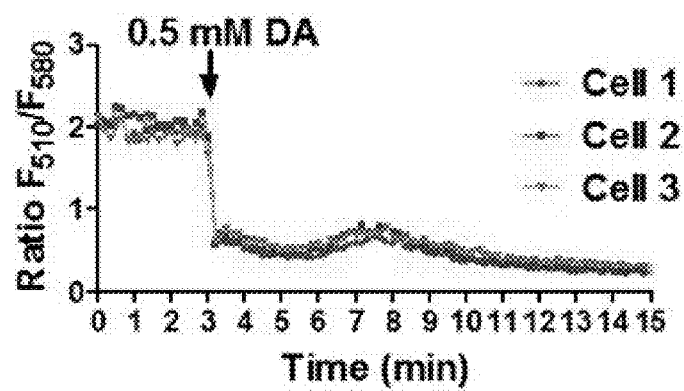
[FIG. 5A]
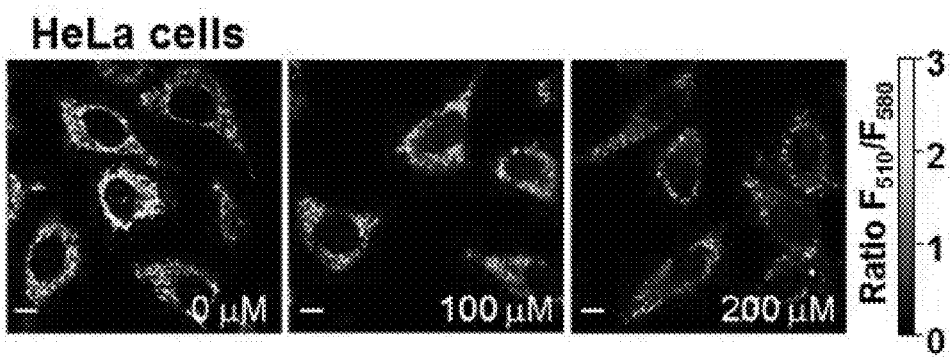

[FIG. 5B]
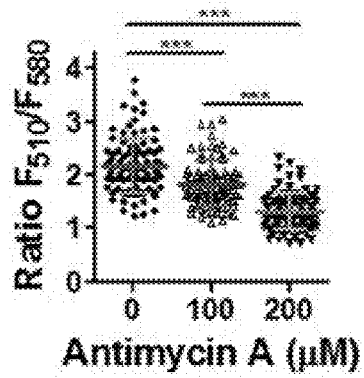
[FIG. 6]
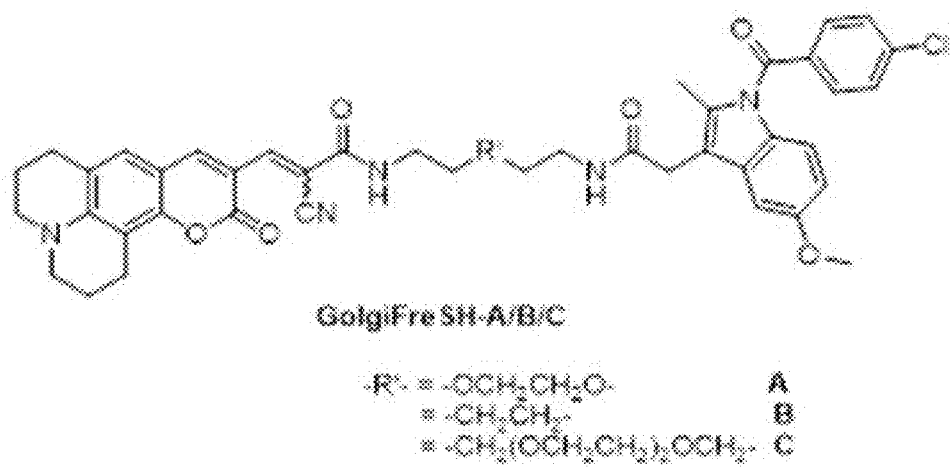

[FIG. 7]
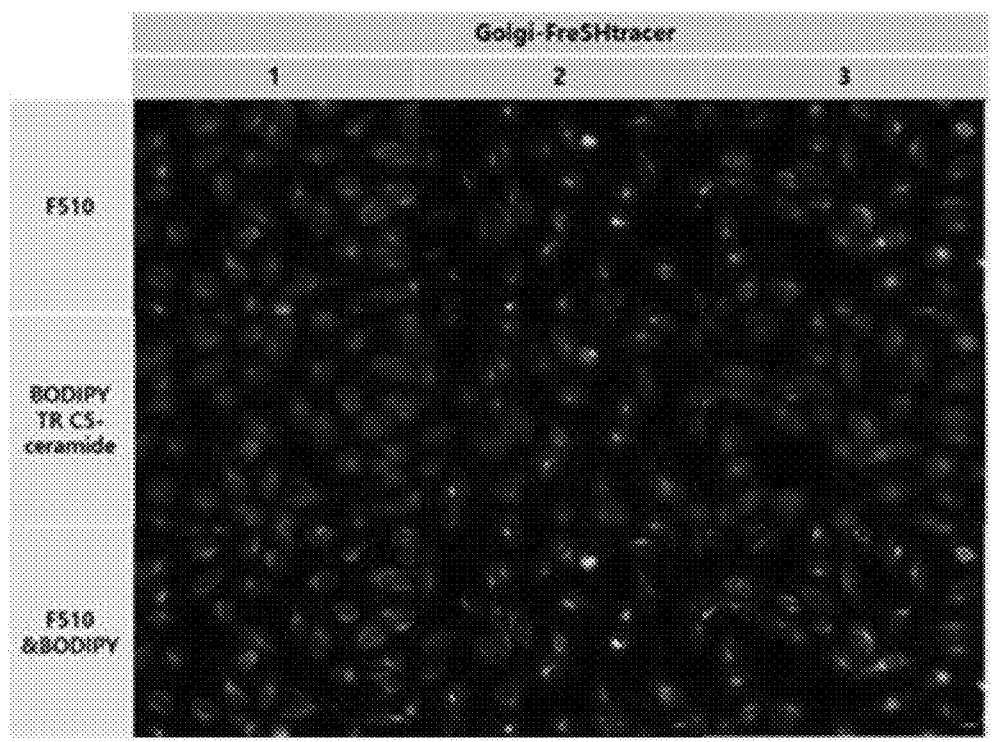
[FIG. 8A]
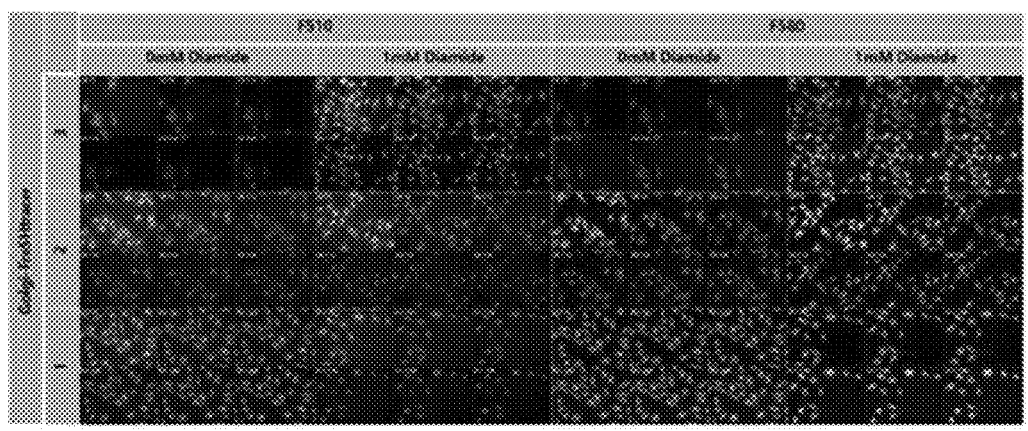

[FIG. 8B]
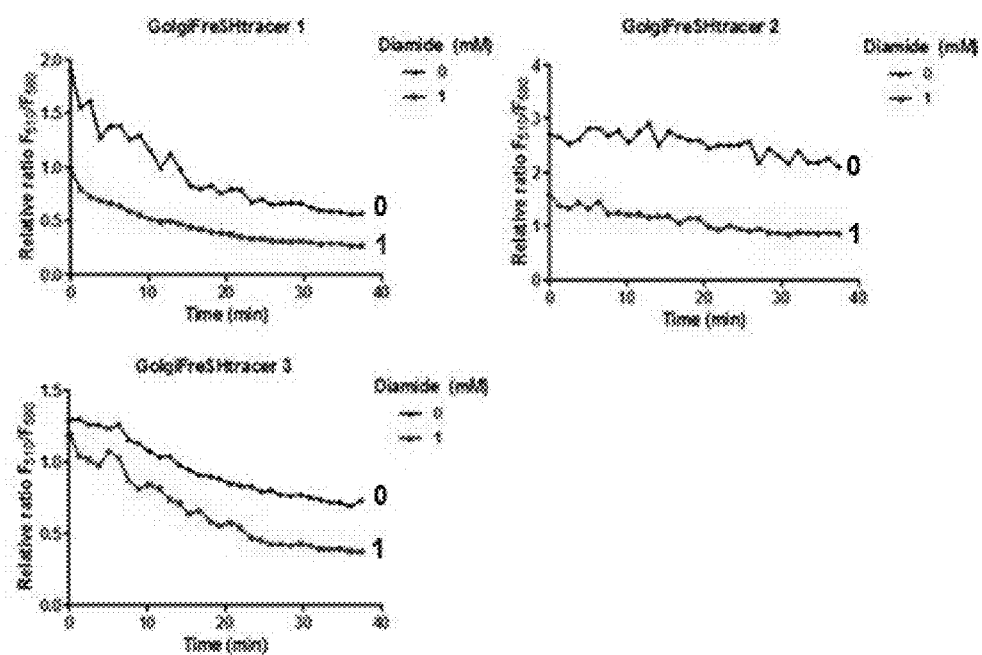

[FIG. 9]
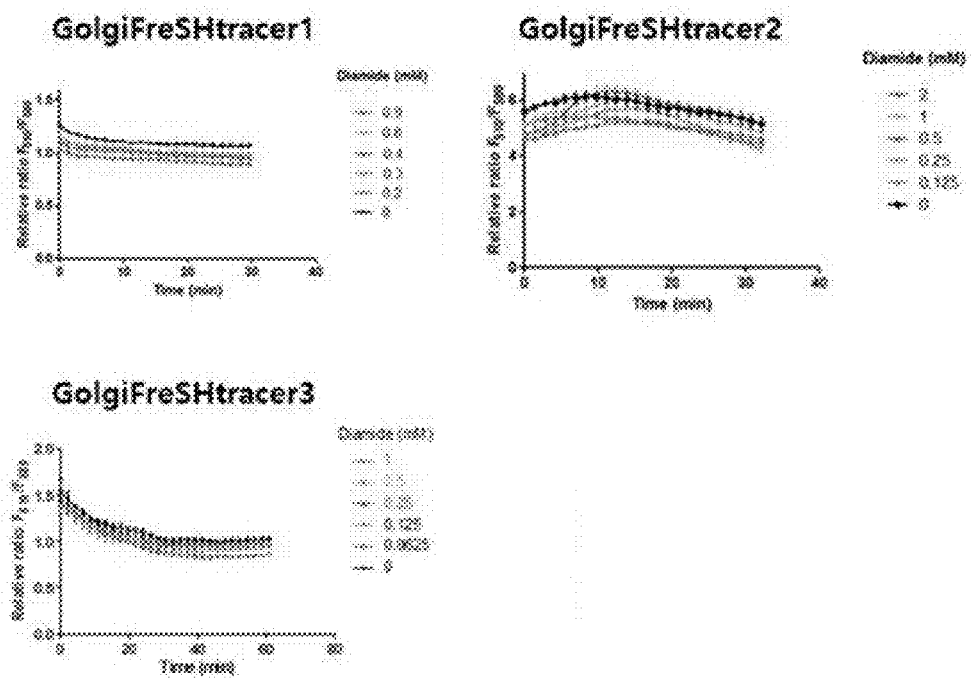

REAL-TIME FLUORESCENCE IMAGING SENSOR FOR MEASURING GLUTATHIONE IN ORGANELLE AND PREPARATION METHOD THEREFOR

CROSS-REFERENCE TO RELATED APPLICATIONS

This application is a U.S. National Stage application of International Patent Application PCT/KR2018/009743, filed Aug. 23, 2018, which claims the benefit of priority of Korean Patent Application no. 10-2017-0107429, filed Aug. 24, 2017.

TECHNICAL FIELD

The present invention relates to a real-time fluorescence imaging sensor for measuring glutathione in cell organelles and a method for fabricating the same. More specifically, the present invention relates to a novel compound for measuring glutathione in cell organelles, a method for preparing the novel compound, a real-time fluorescence imaging sensor for measuring glutathione in cell organelles, which comprises the novel compound, a method for fabricating the imaging sensor, and a method of measuring glutathione in cell organelles by use of the imaging sensor.

BACKGROUND ART

The human body maintains homeostasis by properly eliminating reactive oxygen species (ROS) through the activity of the antioxidant system. However, when the balance between ROS generation and the activity of the antioxidant system is broken, oxidative stress increases, which has recently attracted attention as the primary common cause of development of aging, age-related degenerative diseases, such as degenerative arthritis, cataract, Alzheimer's disease and the like, various cancers, fibrotic diseases, and metabolic syndromes, such as diabetes, obesity, cardiovascular diseases, and the like. The ROS are unstable and highly reactive molecules that oxidize biological molecules to cause biochemical and physiological damage, which is one of the major mechanisms of aging. Thus, not only the degree of oxidation in the human body, but also the degree of antioxidation or antioxidant activity am be used as major biomarkers for measuring biological age.

Meanwhile, mesenchymal stem cells are pluripotent stem cells derived from various adult cells, such as bond mallow cells, umbilical cord blood cells, placental cells (or placental tissue cells), adipose cells (or adipose tissue cells), or the like. For example, mesenchymal stem cells derived from bone marrow have pluripotency to differentiate into adipose tissue, bone/cartilage tissue and muscular tissue, and thus various studies on the development of cell therapeutic agents using mesenchymal stem cells have been conducted.

However, stem cells which are the main component of cell therapeutic agents tend to lose their pluripotency and tissue regeneration ability during culture after isolation and to be aged, and this risk becomes even greater when these cells undergo several passages to obtain a large amount of cells, which corresponds to a therapeutically effective amount. In addition, the amount of stem cells obtained from tissue is very small, and these stem cells need to be used in large amounts, and hence culturing is performed in which the number of stem cells is increased. In recent years, as methods of managing the quality of stem cells by measuring the antioxidant activity of the stem cells, methods of measuring intracellular antioxidant activity have been disclosed (Korean Patent No. 10-1575846; Korean Patent Application Publication No. 2004-0030701; Hongyan Liu et al., Cytotherapy, 14(2); 162-172, 2012).

However, studies on methods of screening high-quality stem cells having high activity by measuring the antioxidant activity of stem cells are still insufficient. Thus, in order to increase the efficiency of use of stem cells which are cell therapy resources having a high scarcity value, there is a need to develop a composition for antioxidant activity measurement which is required to screen highly active stem cells.

In addition, in the measurement of the antioxidant activity of cells, including stem cells, as described above, detection and identification of thiol-containing compounds in biological samples are very important. Consequently, fluorescence methods of effectively detecting thiols in living cells without disrupting the cells have been developed. However, there is a need for compounds for measuring antioxidant activity by measuring thiols from various sources in cells.

DISCLOSURE

Technical Problem

The present inventors have found that the fluorescence intensity of a MitoFreSH-tracer (Mitochondria Fluorescent Real-time SH group-Tracer) or GolgiFreSH-tracer (Golgi Fluorescent Real-time SH group-Tracer) according to the present invention increases or decreases continuously, ratiometrically and reversibly depending on the amount of thiols in mitochondria or Golgi apparatus and that the MitoFreSH-tracer or the GolgiFreSH-tracer can be effectively used as a highly sensitive biosensor for quantitatively or qualitatively detecting the amount of thiols in mitochondria or Golgi apparatus in living cells in real time, thereby completing the present invention.

Therefore, it is an object of the present invention to provide a MitoFreSH-tracer (Mitochondria Fluorescent Real-time SH group-Tracer) represented by any one or more of formulas III to V below, or a GolgiFreSH-tracer (Golgi Fluorescent Real-time SH group-Tracer) represented by any one or more of formulas VII to IX below.

Another object of the present invention is to provide a composition for detecting mitochondrial thiols, which comprises the MitoFreSH-tracer (Mitochondria Fluorescent Real-time SH group-Tracer), or a composition for detecting thiols in Golgi apparatus, which comprises the GolgiFreSH-tracer (Golgi Apparatus Fluorescent Real-time SH group-Tracer).

Still another object of the present invention is to provide a method of screening a thiol enhancer or inhibitor in mitochondria or Golgi apparatus in living cells by use of the MitoFreSH-tracer or the GolgiFreSH-tracer.

These and other objects and advantages of the present invention will become more apparent from the following detailed description of the invention and the appended claims.

However, objects which are to be achieved by the present invention are not limited to the above-mentioned objects, and other objects of the present invention will be clearly understood by those drilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes aid preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least to one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise stated in the specification, all the scientific and technical terms used in the specification have the same meanings as commonly understood by those skilled in the technical field to which the present invention pertains.

As used herein, the term "ratiometric" means that output is directly proportional to input. Specifically, in an embodiment of the present invention, the term "ratiometric" means that the fluorescence intensity or ratio of fluorescence intensity of the composition of the present invention increases or decreases in direct proportion to the input of thiols.

As used herein, the term "detection" means measuring the presence or level of chemical species or biological substances in a sample.

As used herein, the term "reversible" means a state in which a mixture of a reactant and a product in a chemical reaction can produce an equilibrated mixture. More specifically, the term "reversible" means that the compound represented by formula I herein can react reversibly with thiols in an equilibrium state in a forward or reverse direction depending on the amount of the thiols.

As used herein, the term "thiol" means an organic compound containing a carbon-bonded sulfhydryl group. The term "thiol group" is used interchangeably with the term "sulfhydryl group".

In accordance with one aspect of the present invention, the present invention provides a composition for detecting thiols in mitochondria, comprising a compound represented by the following formula I or a salt thereof:

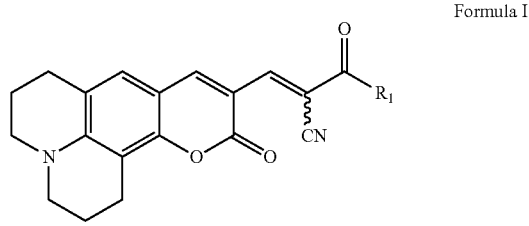

Formula I wherein $R_1$ is a 3- to 7-membered heterocycloalkyl containing one or more N atoms, wherein the heterocycloalkyl has an $R_2$ substituent bonded thereto, wherein $R_2$ is —(C(=O)NH)—(CH$_2$)$_m$—PPh$_3^+$Cl$^-$ (where m is an integer ranging from 1 to 4), —(CF$_2$)$_n$—PPh$_3^+$Cl$^-$ (where n is an integer ranging from 1 to 6), or —(C(=O)—(CH$_2$)$_p$—R$_3$ (where p is an integer ranging from 1 to 4), wherein $R_3$ is —C(NHC(=O)—R$_4$), wherein $R_4$ is a substituent represent by the following formula II:

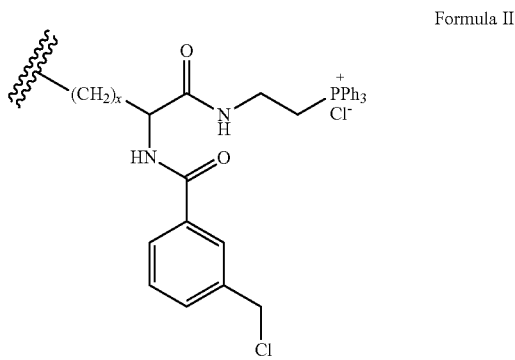

Formula II wherein x is an integer ranging from 1 to 4.

The present inventors have made extensive efforts to develop a highly sensitive biosensor for quantitatively or qualitatively detecting the amount of thiols in mitochondria in cells in real time. As a result, the present inventors have found that the fluorescence intensity of the MitoFreSH-tracer (Mitochondria Fluorescent Real-time SH group-Tracer) represented by formula I according to the present invention increases or decreases continuously, ratiometrically and reversibly depending on the amount of thiols in mitochondria in cells and that the MitoFreSH-tracer can be effectively used as a highly sensitive biosensor for quantitatively or qualitatively detecting the amount of thiols in mitochondria in cells in real time.

As used herein, the term "MitoFreSH-tracer (Mitochondria Fluorescent Real-time SH group-Tracer)" means the compound represented by formula I, which is a coumarin derivative having a cyanoacrylamide electrophile and is used as a fluorescent substance for detecting thiols in mitochondria according to the present invention.

In one embodiment of the present invention, the mitochondria of the present invention are contained in living cells. The composition of the present invention is characterized in that it can measure not only the level of thiols in mitochondria isolated from cells, but also the level of thiols in mitochondria contained in cells. In particular, it can specifically detect the level of thiols in mitochondria in living cells.

In one embodiment of the present invention, $R_1$ in the present invention is a 6-membered heterocycloalkyl containing 1 or 2 N atoms. As used herein, the term "6-membered" included in the "6-membered heterocycloalkyl" does not mean a polycyclic compound, such as a bicyclic compound or a spiro compound, but means a monocyclic 6-membered compound, and the term "heterocycloalkyl" means a non-aromatic cyclic alkyl in which at least one of carbon atoms contained in the ring is substituted with a heteroatom, for example, nitrogen, oxygen or sulfur. In one embodiment, $R_1$ is a 6-membered heterocycloalkyl containing one 1 or 2 nitrogen atoms in the ring.

In one embodiment of the present invention, the compound represented by formula I according to the present invention is any one or more of compounds represented by the following formulas III to V:

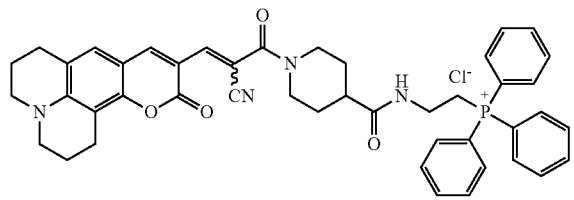

Formula III

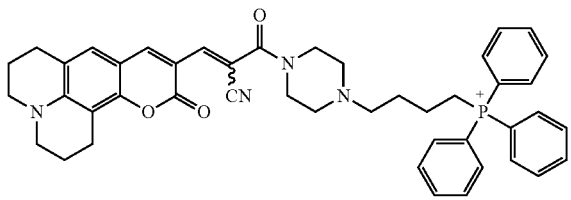

Formula IV

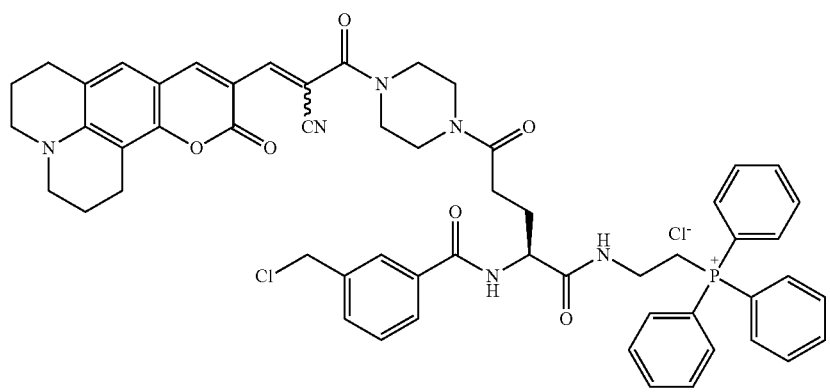

Formula V

The amount of thiols binding to the compound (MitoF-reSH-tracer) represented by any one or more of formulas III to V according to the present invention increases as the amount of thiols in mitochondria in living cells increases. Thus, the fluorescence intensity at 550-680 nm, which is exhibited by the compound in a flee state, decreases, and the fluorescence intensity at 430-550 nm, which is exhibited by the compound in a thiol-bound state, increases. The fluorescence intensity increases or decreases ratiometrically mid reversibly depending on the amount of thiols.

In accordance with another aspect of the present invention, the present invention provides a composition for detecting thiols in Golgi apparatus, comprising a compound represented by the following formula VI or a salt thereof.

ratus in cells in real time. As a result the present inventors have found that the fluorescence intensity of the Golgi-FreSH-tracer (Golgi Fluorescent Real-time SH group-Tracer) represented by formula VI according to the present invention increases or decreases continuously, ratiometrically and reversibly depending on the amount of thiols in Golgi apparatus in cells and that the MitoFreSH-tracer can be effectively used as a highly sensitive biosensor for quantitatively or qualitatively detecting the amount of thiols in Golgi apparatus in cells in real time.

As used herein, the term "GolgiFreSH-tracer (Golgi Fluorescent Real-time SH group-Tracer)" means the compound represented by formula VI, which is a coumarin derivative having a cyanoacrylamide electrophile and is used as a

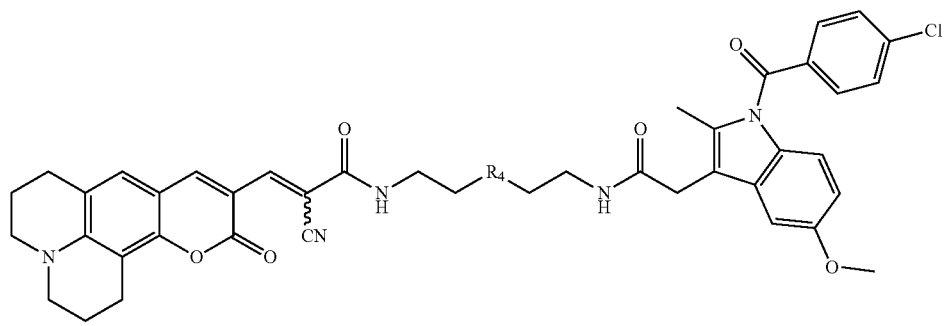

Formula VI wherein $R_4$ is a compound which is $(CH_2)p-(OCH_2CH_2O)q-(CH_2)r$, or $-(CH_2CH_2)s-$, wherein p, q, r and s are each an integer ranging from 1 to 5. More specifically, $R_4$ in formula VI is any one of $(OCH_2CH_2O)-$, $-(CH_2CH_2)-$, and $-(CH_2(OCH_2CH_2)_2OCH_2)-$.

The present inventors haw made extensive efforts to develop a highly sensitive to biosensor for quantitatively or qualitatively detecting the amount of thiols in Golgi appafluorescent substance for detecting thiols in Golgi apparatus according to the present invention.

The amount of thiols binding to the compound (MitoF-reSH-tracer) represented by formula VI according to the present invention increases as the amount of thiols in Golgi apparatus in living cells increases. Thus, the fluorescence intensity at 550-680 nm, which is exhibited by the compound in a flee state, decreases, and the fluorescence intensity at 430-550 nm, which is exhibited by the compound in a thiol-bound state, increases. The fluorescence intensity increases or decreases ratiometrically and reversibly depending on the amount of thiols.

In one embodiment of the present invention, the compound represented by formula VI according to the present invention is any one or more of compounds represented by the following formulas VII to IX:

enantiomer, diastereomer, enantiomeric mixture, or diastereomeric mixture thereof, or a pharmaceutically acceptable sale thereof.

According to one embodiment of the present invention, the compound represented by formula I or VI shows a maximum emission wavelength at 550-680 nm in a free state (i.e., a non-thiol-bound state), and shows a maximum emis-

[Formula VII]

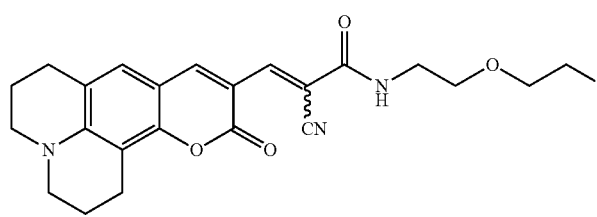
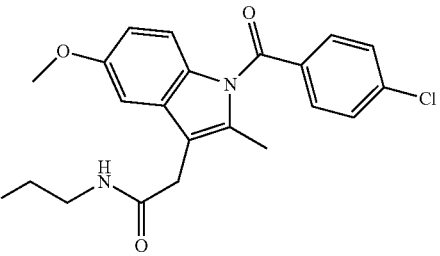

[Formula VIII]

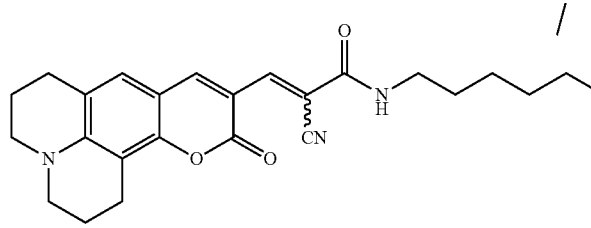

[Formula IX]

When the composition comprising the compound according to the present invention is used, it can measure the antioxidant activity of the organelle mitochondria or Golgi apparatus in all types of cells, including stem cells, thereby accurately measuring cell activity related to the antioxidant activity and screening highly active cells. The measurement of cellular activity by use of the composition of the present invention includes, but is not limited to, the measurement of antioxidant activity.

In one embodiment of the present invention, there is provided a composition for measuring the antioxidant activity of cell organelles, comprising, as an active ingredient, the compound represented by formula I or VI, or a racemate, sion wavelength at 430-550 nm in a thiol-bound state. According to another embodiment of the present invention, the compound represented by formula I or VI according to the present invention shows a maximum emission wavelength at 550-650, 550-620, 550-600, 570-590 or 580 nm in a free state.

According to still another embodiment of the present invention, the compound represented by formula I or VI according to the present invention shows a maximum emission wavelength at 450-550, 470-550, 470-530, 490-530, 500-520 or 510 nm in a thiol-bound state.

According to one embodiment of the present invention, the fluorescence intensity at the emission wavelength of the compound of formula I or VI according to the present invention increases or decreases continuously and reversibly as the amount of thiols in mitochondria increases. According to a more specific embodiment, the fluorescence intensity at the emission wavelength increases or decreases in the range of 430 nm to 680 nm.

According to one embodiment of the present invention, the compound represented by formula I or VI according to the present invention shows a decrease in the fluorescence intensity at 550-680 nm and an increase in the fluorescence intensity at 430-550 nm, as the amount of thiols in mitochondria increases.

According to one embodiment of the present invention, the detection of thiols according to the present invention is performed by obtaining the ratio of the fluorescence intensity at 430-550 nm to the fluorescence intensity at 550-680 nm.

According to me embodiment of the present invention, the ratio in the present invention is a relationship between the fluorescence intensity at 430-550 nm and the fluorescence intensity at 550-680 nm.

According to an embodiment of the present invention, the relationship in the present invention is a mathematical ratio between the fluorescence intensity at 430-550 nm and the fluorescence intensity at 550-680 nm, aid the mathematical ratio increases or decreases ratiometrically and reversibly depending on the amount of thiols in living cells, thereby indicating the amount of thiols in cell organelles in real time.

According to one embodiment of the present invention, the detection according to the present invention is the quantitative or qualitative detection of thiols in the cell organelle mitochondria, Golgi apparatus or nucleus.

According to one embodiment of the present invention, the detection according to the present invention is real-time quantitative detection.

According to one embodiment of the present invention, the detection of thiols in mitochondria, Golgi apparatus or nucleus in the present invention indicates the oxidative stress or degree of oxidation of cells.

According to one embodiment of the present invention, the detection of thiols in mitochondria, Golgi apparatus or nucleus in the present invention indicates the degree of aging of cells.

According to one embodiment of the present invention, the thiols in the present invention include, but are not limited to, glutathione (GSH), homocysteine (Hcy), cysteine (Cys) or any thiols present in the cysteine residues of proteins.

In accordance with still another aspect of the present invention, there is provided a kit for diagnosing an oxidative stress-induced disease, comprising the composition of the present invention. As used herein, the term "oxidative stress-induced disease" means a disease caused by oxidative stress, and has the same meaning as the term "relative oxygen species (ROS)-related disease".

According to an embodiment of the present invention, the oxidative stress-induced disease in the present invention is aging, degenerative arthritis, cataract, Alzheimer's disease, cancer, fibrosis disease, diabetes, obesity, ischemia, ischemic reperfusion injury, inflammation, systemic lupus erythematosus, myocardial infarction, thrombotic stroke, hemorrhagic stroke, bleeding, spinal cord injury, Down syndrome, Crohn's disease, rheumatoid arthritis, uveitis, emphysema, gastric ulcer, oxygen toxicity, tumor, or radiation syndrome.

Advantageous Effects

When the composition comprising the compound according to the presort invention is used, it can measure the antioxidant activity of the organelle mitochondria or Golgi apparatus in living cells, particularly stem cells, and can screen highly active stem cells based on the results obtained by measuring the antioxidant activity of the cell organelle.

DESCRIPTION OF DRAWINGS

FIG. 1 shows the structure of a MitoFreSH-tracer.

FIGS. 2A, 2B, 2C and 2D show experimental results that indicate that a MitoFreSH-tracer reacts reversibly and rapidly with reduced glutathione (a.u.: arbitrary unit; Ex: maximum excitation wavelength; Em: maximum emission wavelength). FIG. 2A shows the reversible reaction of the MitoFreSH-tracer. FIG. 2B shows the results obtained by equilibrating the MitoFreSH-tracer with various concentrations of glutathione ([GSH]0=0-100 mM) for 20 minutes and then measuring the reaction therebetween. The upper panel of FIG. 2B shows the results of measuring the reversible reaction of the MitoFreSH-tracer by the UV-Vis absorption spectrum, and the lower panel of FIG. 2B shows the fluorescence emission spectra of the MitoFreSH-tracer, generated by excitation at 430 nm (lower left of FIG. 2B) and 520 nm (lower right of FIG. 2B), and FIG. 2C is a graph showing the results of monitoring the fluorescence emission spectra at 510 nm (F510) and 580 nm (F580), respectively. FIG. 2D shows the F510/F580 ratio as a function of increasing concentrations of glutathione.

FIG. 3 shows the results of analyzing cell viability at 24 hours after treating HeLa cells with various concentrations of the MitoFreSH-tracer in MTT assay.

FIG. 4 indicates that the level of glutathione in mitochondria in living cells can be imaged with the MitoFreSH-tracer. FIG. 4A show's a confocal microscope fluorescence image of cells loaded with the MitoFreSH-tracer (F510=Ex403-Em525/25; F580=Ex488-Em595/25; scale bar=10 μm), and FIG. 4B shows a confocal microscope fluorescence image of cells loaded with the MitoFreSH-tracer, obtained after treating the cell culture with 0.5 mM diamide (DA) at 3 minutes after the start of microscopic observation of the cells (F510=Ex403-Em525/25; F580=Ex488-Em595/25; scale bar=10 μm), and FIG. 4C shows the results obtained by measuring the fluorescence intensity ratio (arrowhead in FIG. 4A) of each of three cells.

FIG. 5 indicates that the level of glutathione in mitochondria in living cells, which is decreased by reactive oxygen species generated in mitochondria, can be imaged with the MitoFreSH-tracer. FIG. 5A show s a confocal microscope fluorescence image of cells loaded with the MitoFreSH-tracer, obtained after treating the cell culture with antimycin A for 14 hours (F510=Ex403-Em525/25; F580=Ex488-Em595/25; scale bar=10 μm), and FIG. 5B shows the results obtained by measuring the fluorescence intensity ratio of each cell.

FIG. 6 shows the structure of a GolgiFreSH-tracer.

FIG. 7 shows the results of analyzing whether the GolgiFreSH-tracer is distributed in the Golgi apparatus in HeLa cells (F510=Ex403-Em525/25; F580=Ex488-Em595/25; scale bar=10 μm).

FIG. 8 indicates that the level of glutathione in the Golgi apparatus in living cells can be imaged with the GolgiFreSH-tracer. FIG. 8A shows a confocal microscope fluorescence image of cells loaded with the golgiFreSH-tracer (F510=Ex403-Em525/25; BODIPY TR C5-ceramide, Golgi apparatus dye; scale bar=10 μm), and FIG. 8B shows the results of measuring the fluorescence intensity ratio in the image of FIG. 8A.

FIG. 9 indicates that the level of glutathione in the Golgi apparatus in living cells can be quantified with the Golgi-FreSH-tracer.

BEST MODE

When the composition comprising the compound according to the present invention is used, it can measure the antioxidant activity of the organelle mitochondria or Golgi apparatus in living cells, particularly stem cells, and can screen highly active stem cells based on the results obtained by measuring the antioxidant activity of the cell organelle.

Mode for Invention

Hereinafter, the present invention will be described in further detail with reference to examples. However, it will be obvious to those skilled in the art that these examples are for illustrative purposes only and are not intended to limit the scope of the present invention as defined in the appended claims.

Preparation Example 1: Synthesis of Compounds for Measuring Antioxidant Activity of Mitochondria Methods for preparing compounds (MitoFreSH-PPh₃, MitoFreSH-Piperazine and MitoFreSH-Cl) that are used to measure the antioxidant activity of the cell organelle mitochondria are as follows.

1-1. Method for Preparing MitoFreSH-PPh₃ (Formula III)

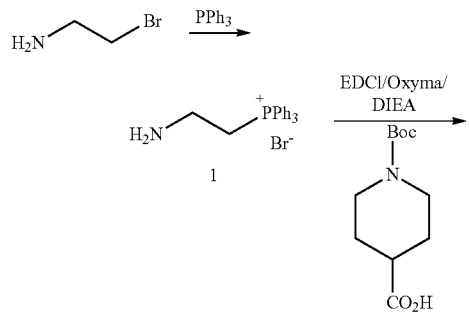

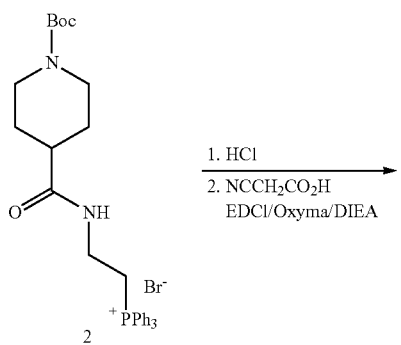

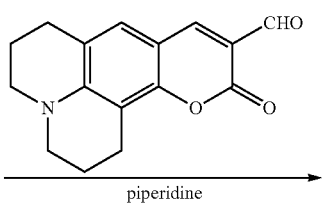

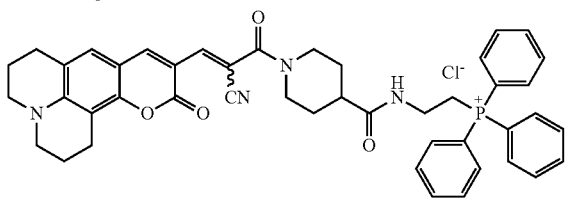

MitoFreSH-PPh₃
(Formula III)

Compound 1

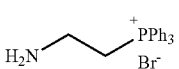

Compound 1

(2-bromoethyl)amine hydrobromide (8.6 g, 42 mmol) and triphenylphosphine (10 g, 38 mmol) were dissolved in 50 mL of CH₃CN, and the solution was heated and refluxed for 18 hours, and then cooled to room temperature. The solvent was removed by distillation under reduced pressure, and the remaining mixture was dissolved in distilled water and adjusted to a pH of 11 by addition of a saturated aqueous solution of K₂CO₃. The mixture was extracted with CHCl₃, and the extract was dried with Na₂SO₄, and then filtered. The filtrate was distilled under reduced pressure to remove the solvent. The remaining solid was washed with Et₂O, and then dried under reduced pressure to obtain compound 1 (10 g, 68%).

$^1$H NMR (400 MHz, CDCl₃): a (ppm)=7.66-7.87 (m, 15H), 4.01-4.08 (m, 2H), 3.15-3.21 (m, 2H), 2.67 (s, 2H).
$^{31}$P NMR (121 MHz, CDCl₃): a (ppm)=24.60.

Compound 2

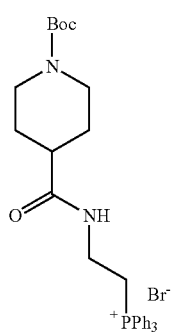

Compound 2

1-(tert-butoxycarbonyl)-4-piperidinecarboxylic acid (0.15 g, 0.65 mmol), oxyma (0.10 g, 0.71 mmol), N,N-diisopropylethylamine (DIEA: 0.33 mL, 1.9 mmol), 1-ethyl-3-(3-dimethylaminopropyl)-carbodiimide (EDCI; 0.12 g, 0.71 mmol) and compound 1 (0.21 g, 0.54 mmol) were dissolved in 3 mL of N,N-dimethylformamide (DMF), and the solution was stirred at room temperature for 11 hours. The solvent was removed by distillation under reduced pressure, and the remaining mixture w as purified by $SiO_2$ column chromatography (MeOH/$CH_2Cl_2$ 6/94) to obtain compound 2 as a yellow solid (021 g, 63%).

$^1$H NMR (400 MHz, $CDCl_3$): a (ppm)=8.90-8.93 (t, J=5.7 Hz, 1H), 7.69-7.85 (m, 15H), 4.07 (br s, 2H), 3.69-3.80 (m, 4H), 2.73 (br s, 2H), 2.34-2.42 (m, 1H), 1.75-1.78 (d, J=11.6 Hz, 1H), 1.51-1.55 (m, 1H), 1.44 (s, 9H).

Compound 3

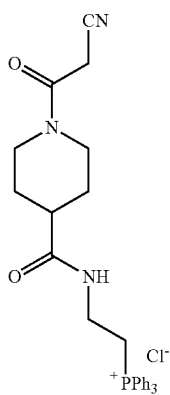

Compound 2 (0.14 g, 0.23 mmol) was dissolved in a 4 M solution of HCl/dioxane and then stirred at room temperature for 1 hour. The solvent was removed by distillation under reduced pressure, and the remaining compound was used in the next reaction without purification.

$^1$H NMR (400 MHz, $CDCl_3$): a (ppm)=9.66 (br s, 1H), 9.17 (br s, 1H), 9.00 (br s, 2H), 7.73-7.85 (m, 15H), 3.74-3.79 (m, 2H), 3.63-3.67 (m, 2H), 3.38 (br s, 2H), 2.96 (br s, 2H), 2.49 (br s, 1H), 2.28 (br s, 2H), 2.06 (br s, 2H).

The above compound, cyanoacetic acid (21 mg, 0.25 mmol), oxyma (35 mg, 0.25 mmol), DIEA (0.15 mL, 0.83 mmol) and EDCI (47 mg, 0.25 mmol) were dissolved in 1 mL of DMF, and the solution was stirred at room temperature for 14 hours. The solvent was removed by distillation under reduced pressure, and the remaining mixture was purified by column chromatography (MeOH/$CH_2Cl_2$ 8/92) to obtain compound 3 as a yellow solid (49 mg, 45%).

$^1$H NMR (400 MHz, $CDCl_3$): a (ppm)=9.47-9.49 (t, J=5.8 Hz, 1H), 7.70-7.86 (m, 15H), 4.43-4.56 (d, J=13.3 Hz, 1H), 3.66-3.82 (m, 4H), 3.51 (s, 2H), 3.16-3.23 (m, 1H), 2.71-2.78 (m, 1H), 2.54-2.62 (m, 1H), 1.94-1.97 (d, J=14.4 Hz, 1H), 1.82-1.85 (d, J=11.2 Hz, 1H), 1.64-1.75 (m, 1H), 1.52-1.62 (m, 1H), 1.43-1.47 (m, 1H).

MitoFreSH-PPh$_3$ (Formula III)

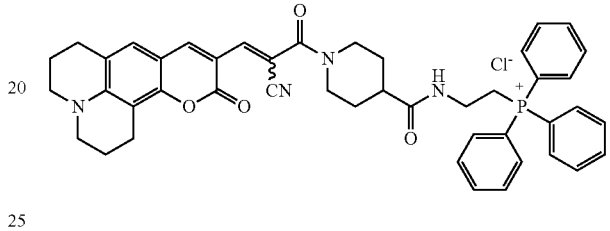

10-oxo-2,3,5,6-tetrahydro-1H,4H,10H-11-oxa-3a-azabenzo

[de]anthracene-9-carbaldehyde (36 mg, 0.13 mmol), compound 3 (70 mg, 0.13 mmol) and piperidine (13 μL, 0.13 mmol) were dissolved in 1 mL of 2-propanol, and the solution was healed at 60° C. for 1 hour, and then cooled to room temperature. The solvent was removed by distillation under reduced pressure, and the remaining mixture was purified by $SiO_2$ column chromatography (MeOH/$CH_2Cl_2$ 5/95) to obtain the compound (MitoFreSH-PPh$_3$) as a red solid (36 mg, 36%).

$^1$H NMR (400 MHz, $CDCl_3$): a (ppm)=9.44 (br s, 1H), 9.36 (brs, 1H), 8.63 (s, 1H), 7.89 (s, 1H), 7.71-7.84 (m, 15H), 7.50 (s, 1H), 6.99 (s, 1H), 6.84 (s, 1H), 3.62-3.88 (m, 4H), 3.32-3.38 (m, 4H), 2.84-2.88 (m, 2H), 2.75-2.78 (m, 2H), 2.53-2.60 (m, 1H), 1.96-2.04 (m, 4H), 1.88-1.95 (m, 4H), 1.62-1.71 (m, 4H).

1-2. Synthesis of MitoFreSH-Piperazine (Formula IV)

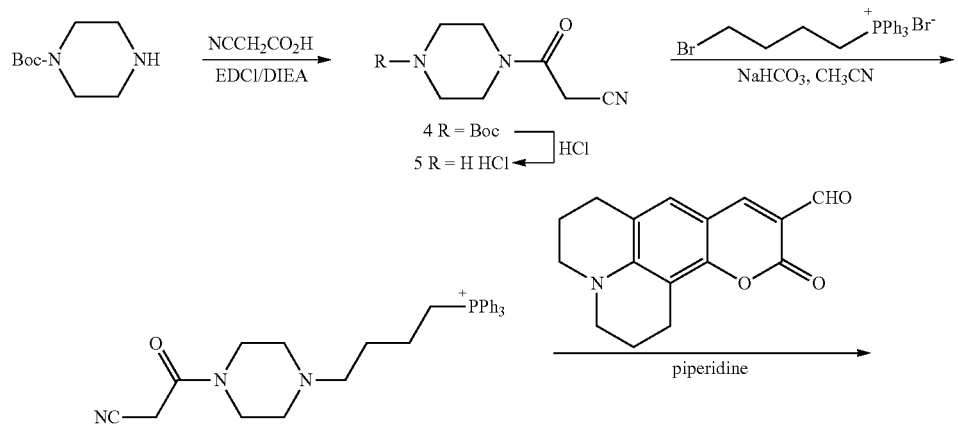

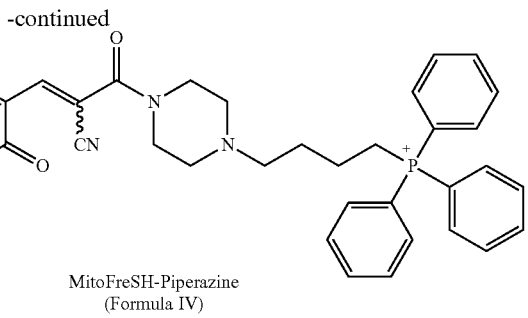

MitoFreSH-Piperazine
(Formula IV)

Compound 4

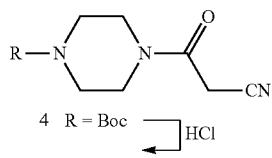

Tert-butyl piperazine-1-carboxy late (1.0 g, 5.3 mmol) and cyanoacetic acid (0.54 g, 1.2 eq.) were dissolved in 10 mL of DMF, and DIEA (3.28 mL, 3.5 eq.) and EDCI (136 g, 1.5 eq.) were added to the solution. After stirring at room temperature for 12 hours, the solvent was removed by distillation under reduced pressure. The remaining mixture was purified by SiO$_2$ column chromatography to obtain compound 4 as a white solid (1.13 g, 84%).

$^1$H NMR (400 MHz, CDCl$_3$): a (ppm)=3.60 3.64 (m, 2H), 3.50 3.55 (m, 2H), 3.51 (s, 2H), 3.43 3.48 (m, 4H), 1.47 (s, 9H); HRMS (m/z): [M+H]+ 254.1496.

Compound 5

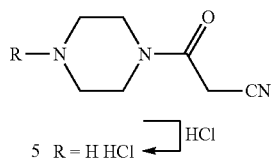

Compound 4 (0.30 g, 12 mmol) was dissolved in 5 mL of a 4 M solution of HCl/dioxane, and then stirred at room temperature for 1 hour. The solvent was removed by distillation under reduced pressure, and the remaining compound 5 was used in the next reaction without purification.

$^1$H NMR (400 MHz, DMSO-d6): a (ppm)=9.54 (br s, 2H), 4.12 (s, 2H), 3.67 3.70 (m, 2H), 3.58 3.61 (m, 2H), 3.04 3.12 (m, 4H).

Compound 6

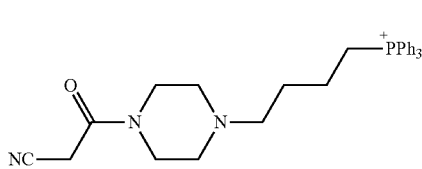

Compound 5 (0.15 mmol) and (4-bromobutyl)triphenylphosphonium bromide (0.15 g, 0.30 mmol) were dissolved in 1 mL of acetonitrile (CH$_3$CN), and sodium hydrogen carbonate (NaHCO$_3$, 64 mg, 0.7545 mmol) was added to the solution. After stirring at 50° C. for 20 hours, the solvent was removed by distillation under reduced pressure. The remaining mixture was purified by SiCh column chromatography (MeOH/CH$_2$Cl$_2$ 15/85) to obtain compound 6 as a white solid (71 mg, 71%).

$^1$H NMR (400 MHz, CDCl$_3$): a (ppm)=7.69-7.88 (m, 15H), 3.78-3.86 (m, 2H), 3.71 (s, 2H), 3.51-3.53 (t, J=4.7 Hz, 2H), 3.47-3.49 (t, J=4.7 Hz, 2H), 2.54-2.56 (t, J=4.1 Hz, 2H), 2.46-2.49 (t, J=6.5 Hz, 2H), 2.38-2.40 (t J=5.1 Hz, 2H), 1.85-1.91 (m, 2H), 1.66-1.74 (m, 2H).

MitoFreSH-Piperazine (Formula IV)

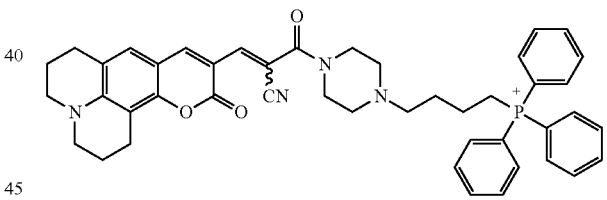

10-oxo-2 3,5,6-tetrahydro-1H,4H,10H-11-oxa-3a-azabenzo[de]anthracene-9-carbaldehyde (35 mg, 0.13 mmol), compound 6 (64 mg, 0.12 mmol) and piperidine (12 μL, 0.12 mmol) were dissolved in 1 mL of 2-propanol, aid the solution was stirred at 60° C. for 1 hour, and then cooled to room temperature. The solvent was removed by distillation under reduced pressure, and the remaining mixture was purified by SiO$_2$ column chromatography (MeOH/CH$_2$Cl$_2$ 6/94) to obtain the compound MitoFreSH-Piperazine as a red solid (61 mg, 66%).

$^1$H NMR (400 MHz, CDCl$_3$): a (ppm)=8.61 (s, 1H), 7.69-7.91 (m, 15H), 7.45 (s, 1H), 7.00 (s, 1H), 6.86 (s, 1H), 3.56 (br s, 4H), 3.35-3.39 (q, J=5.9 Hz, 4H), 2.84-2.88 (t, J=6.5 Hz, 2H), 2.75-2.78 (t, J=6.3 Hz, 2H), 2.41-2.49 (m, 4H), 1.84-2.04 (m, 12H).

1-3. Synthesis of MitoFreSH-Cl(Formula V)
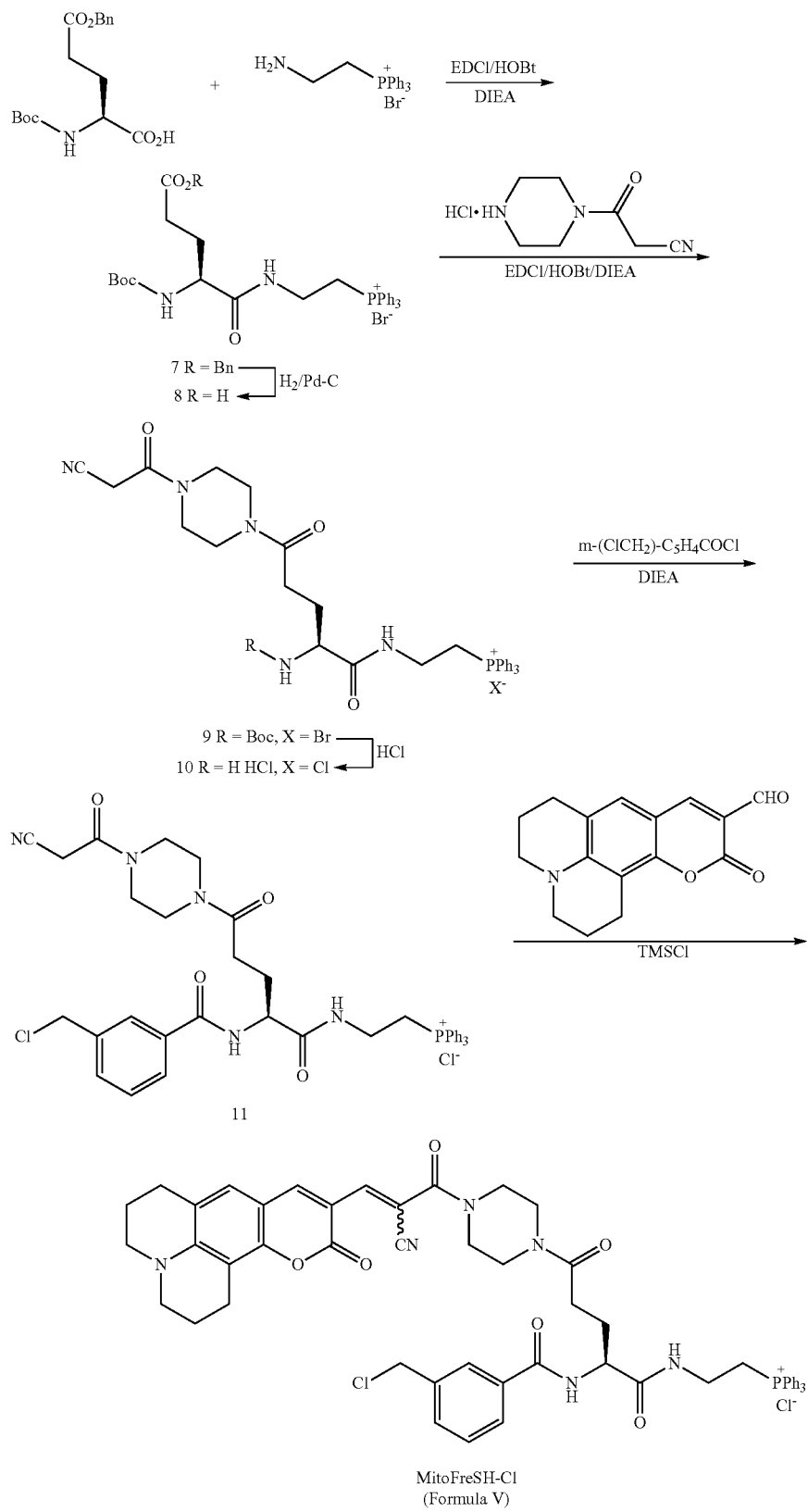
MitoFreSH-Cl
(Formula V)

Compound 7

5-benzyl N-(tert-butoxycarbonyl)-L-glutamate (0.10 g, 029 mmol), 1-hydroxybenzotriazole (HOBt, 80 mg, 2.0 eq.) and DIEA (0.18 mL, 3.5 eq.) were dissolved in 1 mL of DMF, and EDCI (0.11 g, 2.0 eq.) and compound 1 (0.13 g, 12 eq.) were added to the solution. After stirring at room temperature for 16 hours, the solution was diluted with ethyl acetate (EtOAc), and then washed with a 0.5 M aqueous solution of citric add, a saturated aqueous solution of sodium hydrogen carbonate ($NaHCO_3$) and a saturated aqueous solution of sodium chloride (NaCl). The organic layer was separated, dried with sodium sulfate ($Na_2SO_4$), and then filtered, and the filtrate to was distilled under reduced pressure to remove the solvent. The remaining mixture was purified by $SiO_2$ column chromatography to obtain compound 4 as a white solid (0.16 g, 76%). $^1$H NMR (400 MHz, $CDCl_3$): δ (ppm)=9.49 (brs, 1H), 7.68 7.83 (m, 15H), 7.27 7.35 (m, 5H), 5.87 (d, J=9.2 Hz, 1H), 5.08 (s, 2H), 4.18 4.23 (m, 1H), 3.61 3.87 (m, 4H), 2.43 2.47 (m, 2H), 2.12 2.22 (m, 1H), 1.94 2.01 (m, 1H), 1.43 (s, 9H); $^{13}$CNMR (100 MHz, $CDCl_3$): δ (ppm)=172.8, 172.7, 155.2, 135.8, 135.3 (d, $^4J_{CP}$=3.0 Hz), 133.4 (d, $^3J_{CP}$=10.4 Hz), 130.5 (d, $^2J_{CP}$=12.7 Hz), 128.4, 128.1, 128.0, 117.4 (d, $^1J_{CP}$=85.9 Hz), 79.2, 66.1, 53.9, 33.3, 30.4, 28.4, 28.3, 22.2 (d, $^1J_{CP}$=49.7 Hz); $^{31}$P NMR (121 MHz, $CDCl_3$): δ (ppm)= 22.1; HRMS (m/z): [M]$^+$625.2826.

Compound 8

Compound 7 (12 g, 1.7 mmol) was dissolved in 5 mL of methanol ($CH_3OH$) and 5 mL of distilled water, aid 10% Pd—C (0.12 g) was added to the solution, followed by stirring in a reactor under an atmosphere of $H_2$ gas (1 atm) for 12 hours. The solution was filtered through celite, and the filtrate was distilled under reduced pressure to remove the solvent. The remaining compound 8 (1.04 g, 99%) was used in the next reaction without purification. $^1$H NMR (400 MHz, $CDCl_3$): δ (ppm)=8.95 (br s, 1H), 7.70 7.82 (m, 15H), 5.97 (br s, 1H), 4.16 (br s, 1H), 3.60 3.90 (m, 4H), 2.35 2.45 (m, 2H), 1.95 2.05 (m, 2H), 1.37 (s, 9H); $^{31}$P NMR (121 MHz, $CDCl_3$): δ (ppm)=22.1.

Compound 9

Compound 8 (0.15 g, 0.24 mmol), compound 5 (49 mg, 1.05 eq.) and DIEA (0.15 mL, 3.5 eq.) were dissolved in 2 mL of DMF, and HOBt (3 mg, 0.1 eq.) and EDCI (95 mg, 2.0 eq.) were added to the solution. After stirring at room temperature for 4 hours, the solvent was removed by distillation under reduced pressure, and the remaining mixture was purified by $SiO_2$ column chromatography to obtain compound 9 as a yellow solid (0.14 g, 78%). $^1$H NMR (400 MHz, $CDCl_3$): δ (ppm)=major conformer) 9.46 (br s 1H), 7.72 7.84 (m, 15H), 5.79 (d, J=7.8 Hz, 1H), 4.15 4.21 (m, 1H), 3.47 3.79 (m, 14H), 2.50 2.60 (m, 2H), 2.12 2.15 (m, 1H), 2.00-2.04 (m, 1H), 1.42 (s, 9H); $^{13}$CNMR (100 MHz, $CDCl_3$): δ (ppm)=(*major conformer; minor conformer) 172.8, 172.7*, 1712**, 171.0*, 161.1, 155.2, 135.3, 133.4 (d, $^3J_{CP}$=10.3 Hz), 130.5 (d, $^2J_{CP}$=12.7 Hz), 117.4 (d, $^1J_{CP}$=85.8 Hz), 114.5, 79.2, 54.0, 46.3*, 45.8**, 45.3*, 44.7, 42.2, 41.9*, 412**, 40.8*, 33.3, 30.0**, 29.5*, 29.2*, 28.9**, 28.3, 25.4, 2.22 (d, $^1J_{CP}$=49.8 Hz); $^{31}$P NMR (121 MHz, $CDCl_3$): δ (ppm)=22.1; HRMS (m/z): [M]$^+$ 670.3157.

Compound 10

Compound 9 (0.23 g, 0.31 mmol) was dissolved in 3 mL of a 4 M solution of HCl/dioxane, and then stirred at room temperature fix 1 hour. The solvent was removed by distillation under reduced pressure, and the remaining compound 10 was used in the next reaction without purification. $^1$H NMR (400 MHz, DMSO-$d_6$): δ (ppm)=9.44 (d, J=6.1 Hz, 1H), 8.49 (brs, 3H), 7.76 7.94 (m, 15H), 4.09 4.11 (m, 1H), 3.80 3.84 (m, 1H), 3.33 3.50 (m, 12H), 2.50 2.55 (m, 2H), 1.94 1.98 (m, 2H); $^{31}$P NMR (121 MHz, DMSO-$d_6$): δ (ppm)=22.4.

Compound 11

Compound 10 (0.10 g, 0.15 mmol) and 3-(chloromethyl) benzoyl chloride (25 μL, 1.05 eq.) were dissolved in 1 mL of $CH_2Cl_2$, and DIEA (58 μL, 2.0 eq.) was added to the solution. After stirring at room temperature for 1 hour, the solvent was removed by distillation under reduced pressure, and the remaining mixture was purified by $SiO_2$ column chromatography to obtain compound 11 as a white solid (0.10 g, 85%). $^1$H NMR (400 MHz, $CDCl_3$): δ (ppm)= (major conformer) 9.65 (br s, 1H), 8.33 (d, J=8.3 Hz, 1H), 8.13 (s, 1H), 8.05 (d, J=7.8 Hz, 1H), 7.69 7.82 (m, 15H), 7.52 (d, J=7.9 Hz, 1H), 7.42 7.46 (m, 1H), 4.74 4.79 (m, 1H), 4.65 (s, 2H), 3.35 3.74 (m, 14H), 2.53 2.60 (m, 2H), 2.25 2.30 (m, 2H); $^{13}$C NMR (100 MHz, $CDCl_3$): δ (ppm)= (*major conformer. minor conformer) 173.1, 173.0*, 171.3*, 171.2**, 166.4, 160.9, 137.7, 135.5, 134.1, 133.5 (d, $^3J_{CP}$=10.3 Hz), 131.7, 130.6 (d, $^2J_{CP}$=12.7 Hz), 128.9, 128.3*, 1282**, 127.8*, 127.7**, 117.5 (d, $^1J_{CP}$=85.9 Hz), 114.5, 54.2, 46.3*, 45.9, 45.8**, 45.3*, 44.8, 42.1, 42.0*, 41.3**, 41.0*, 302**, 29.7*, 28.3*, 28.0**, 25.3, 22.3 (d, $^1J_{CP}$=49.8 Hz); $^{31}$P NMR (121 MHz, $CDCl_3$): δ (ppm)=222; HRMS (m/z): [M]$^+$722.2662.

MitoFreSH-Cl(Formula V)

Compound 11 (0.12 g, 0.16 mmol) and 10-oxo-2,3,5,6-tetrahydro-1H,4H,10H-11-oxa-3a-azabenzo[de]-anthracene-9-carbaldehyde (46 mg, 1.1 eq.) were dissolved in 1 mL of DMF, and chlorotrimethylsilane (60 μL, 3.0 eq.) was added to the solution, followed by stirring at 130° C. for 5 HOUR. After cooling to room temperature, foe solvent was removed by distillation under reduced pressure, and foe remaining mixture was purified by $SiO_2$ column chromatography to obtain the compound MitoFreSH-Cl as a red solid (79 mg, 50%). $^1$H NMR (400 MHz, $CDCl_3$): δ (ppm)= (major conformer) 9.58 (br s, 1H), 8.63 (s, 1H), 8.40 (d, J=7.4 Hz, 1H), 7.72 8.21 (m, 18H), 7.51 (d, J=7.0 Hz, 1H), 7.42 7.45 (m, 1H), 7.00 (s, 1H), 4.74 4.80 (m, 1H), 4.60 (s, 2H), 3.58 3.73 (m, 12H), 3.33 3.38 (m, 4H), 2.83 2.87 (m, 2H), 2.72 2.78 (m, 2H), 2.55 2.58 (m, 2H), 2.27-2.31 (m, 2H), 1.97 2.04 (m, 4H); $^{13}$C NMR (100 MHz, $CDCl_3$): δ (ppm)=(major conformer) 172.9, 171.1, 166.2, 163.9, 161.3, 152.5, 149.0, 145.9, 142.8, 137.6, 135.4, 134.0, 133.4 (d, $^3J_{CP}$=10.3 Hz), 131.6, 130.6 (d, $^2J_{CP}$=12.7 HZ), 128.8, 128.2, 127.7, 127.5, 119.9, 117.4 (d, $^1J_{CP}$=85.9 Hz), 117.1, 109.7, 108.2, 106.0, 100.4, 54.2, 50.4, 49.9, 45.9, 45.1 (br), 41.2 (br), 33.4, 29.9, 28.0, 27.2, 22.2 (d, $^1J_{CP}$=50.0 Hz), 20.9, 19.9, 19.8; $^{31}$P NMR (121 MHz, $CDCl_3$): δ (ppm)= 22.2; HRMS (m/z): [M]$^+$ 973.3616.

Preparation Example 2: Synthesis of Compounds for Measuring Antioxidant Activity of Golgi Apparatus Methods for preparing compounds (GolgiFreSH-tracers; GolgiFreSH-A/B/C) that are used to measure the antioxidant activity of the cell organelle Golgi apparatus are as follows:

21
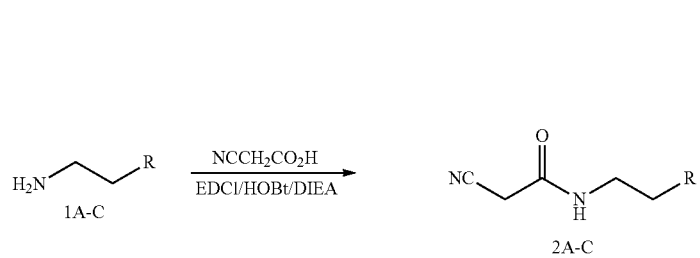
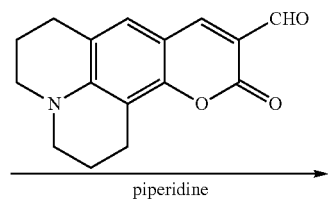
-R = -(OCH₂CH₂)₂NHCO₂C(CH₃)₃  A
   = -(CH₂)₄NHCO₂C(CH₃)₃  B
   = -CH₂(OCH₂CH₂)₃CH₂NHCO₂C(CH₃)₃  C
22
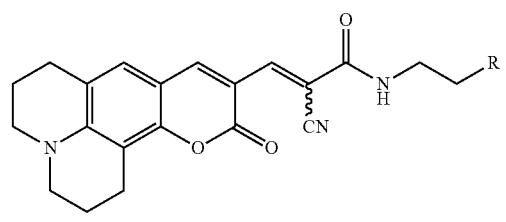
3A-C
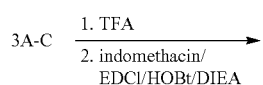
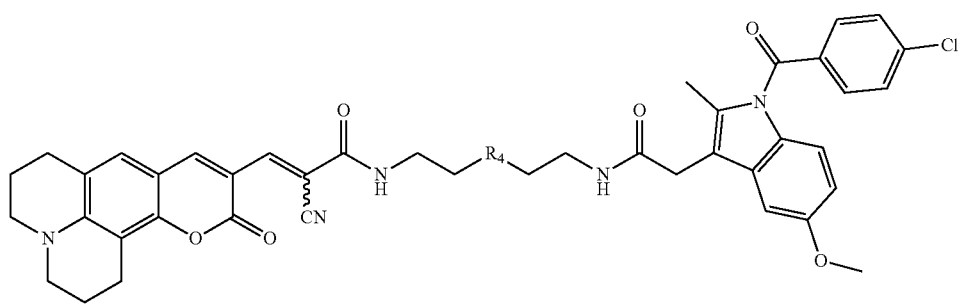
GolgiFreSH-A/B/C
-R₄- = -OCH₂CH₂O-  A
     = -CH₂CH₂-  B
     = -CH₂(OCH₂CH₂)₂OCH₂-  C The GolgiFreSH-A/B/C compounds are classified by $R_4$ as shown in Table 1 below.
TABLE 1
| $R_4$ | Compound |
|---|---|
| A | Formula VII (GolgiFreSH-tracer 1) |
| B | Formula VIII (GolgiFreSH-tracer 2) |
| C | Formula IX (GolgiFreSH-tracer 3) |
The structures of GolgiFreSH-tracers 1 to 3 are as follows.
[GolgiFreSH-Tracer 1, Formula VII]
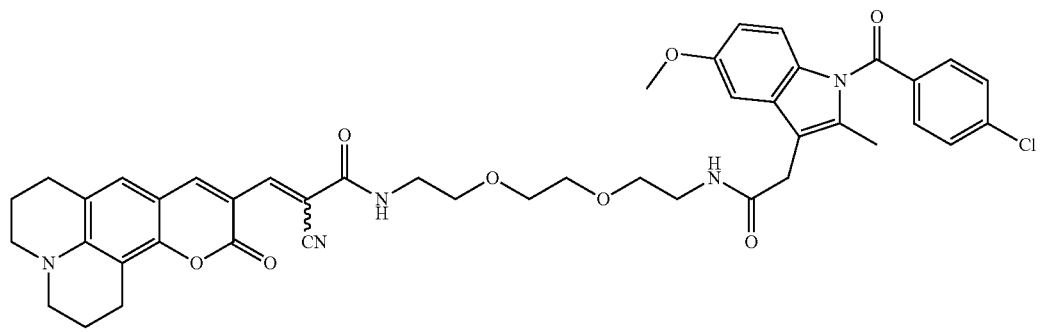 [SMILES: COc1ccc2c(c1)c(CC(=O)NCCOCCOCCNC(=O)C(C#N)=Cc1cc3cc4c5c(c3oc1=O)CCCN5CCC4)c(C)n2C(=O)c1ccc(Cl)cc1]
[GolgiFreSH-Tracer 2, Formula VIII]
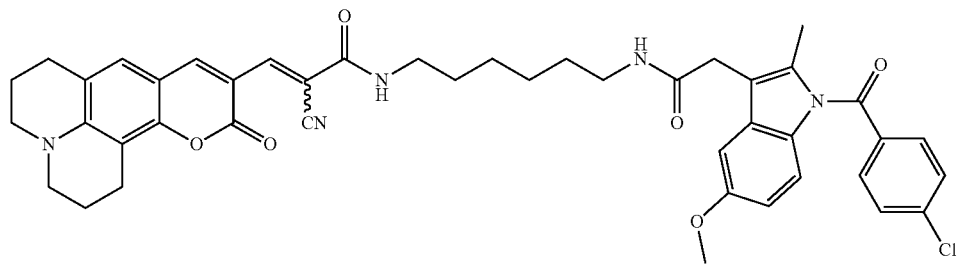 [SMILES: COc1ccc2c(c1)c(CC(=O)NCCCCCCNC(=O)C(C#N)=Cc1cc3cc4c5c(c3oc1=O)CCCN5CCC4)c(C)n2C(=O)c1ccc(Cl)cc1]
[GolgiFreSH-Tracer 3, Formula IX]
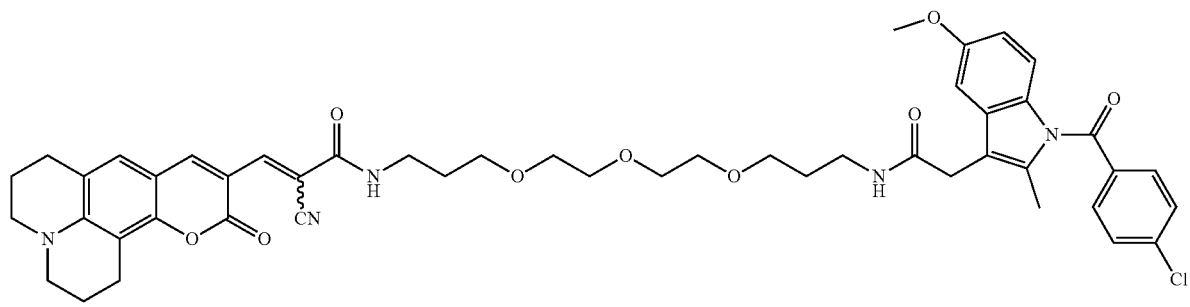 [SMILES: COc1ccc2c(c1)c(CC(=O)NCCCOCCOCCOCCCNC(=O)C(C#N)=Cc1cc3cc4c5c(c3oc1=O)CCCN5CCC4)c(C)n2C(=O)c1ccc(Cl)cc1]

Compound 2

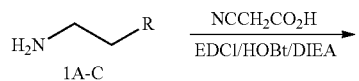

Compound 3

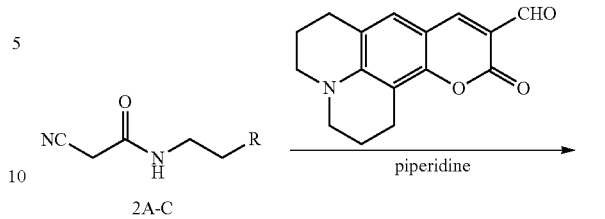

-R = -(OCH$_2$CH$_2$)$_2$NHCO$_2$C(CH$_3$)$_3$  A
= -(CH$_2$)$_4$NHCO$_2$C(CH$_3$)$_3$  B
= -CH$_2$(OCH$_2$CH$_2$)$_3$CH$_2$NHCO$_2$C(CH$_3$)$_3$  C

Compound 1, cyanoacetic acid (1.2 eq.), 1-hydroxybenzotriazol (HOBt; 1.5 eq.), N,N-diisopropylethylamine (DIEA; 2.0 eq.) and 1-ethyl-3-(3-dimethylaminopropyl)-carbodiimide (EDCI; 2.5 eq.) were dissolved in N,N-dimethylformamide (DMF), and the solution was stirred at room temperature for 15 to 20 hours. The solvent was removed by distillation under reduced pressure, and the remaining mixture was diluted with ethyl acetate (EtOAc) and then washed with a saturated aqueous solution of sodium chloride (NaCl). The organic layer was separated, dried with sodium sulfate (Na$_2$SO$_4$), and then filtered, and the filtrate was distilled under reduced pressure to remove the solvent. The remaining mixture was purified by SiO$_2$ column chromatography to obtain compound 2.

Compound 2A $^1$H NMR (500 MHz, CDCl$_3$): a (ppm)= 6.73 (br, 1H), 4.96 (br, 1H), 3.57-3.69 (m, 8H), 3.31 (m, 2H), 3.41 (s, 2H), 3.34 (m, 2H), 1.45 (s, 9H).

Compound 2B $^1$H NMR (500 MHz, DMSO-d6): a (ppm)= 8.19 (t, J=52 Hz, 1H), 6.79 (t, J=5.6 Hz, 1H), 3.59 (s, 2H), 3.01 (m, 2H), 2.88 (m, 2H), 1.37 (s, 9H), 1.33-1.39 (m, 4H), 1.22-124 (m, 4H).

Compound 2C $^1$H NMR (500 MHz, CDCl$_3$): a (ppm)= 7.18 (br, 1H), 4.90 (br, 1H), 3.62-3.69 (m, 8H), 3.60 (m, 2H), 3.53 (t, J=6.0 Hz, 2H), 3.45 (m, 2H), 3.37 (s, 2H), 3.22 (m, 2H), 1.82 (m, 2H), 1.76 (m, 2H), 1.44 (s, 9H).

-R = -(OCH$_2$CH$_2$)$_2$NHCO$_2$C(CH$_3$)$_3$  A
= -(CH$_2$)$_4$NHCO$_2$C(CH$_3$)$_3$  B
= -CH$_2$(OCH$_2$CH$_2$)$_3$CH$_2$NHCO$_2$C(CH$_3$)$_3$  C 10-oxo-2,3,5,6-tetrahydro-1H,4H,10H-11-oxa-3a-azabenzo[de]anthracene-9-carbaldehyde, compound 2 (1.0 eq.) and piperidine (1.0 eq.) were dissolved in 2-propanol, and the solution was heated at 60° C. for 2 to 4 hours, and then coded to room temperature. The solvent was removed by distillation under reduced pressure, and the remaining mixture was purified by SiO$_2$ column chromatography to obtain compound 3.

Compound 3A $^1$H NMR (500 MHz, CDCl$_3$): a (ppm)= 8.62 (s, 1H), 8.55 (s, 1H), 7.00 (s, 1H), 6.67 (br, 1H), 5.08 (br, 1H), 3.62-3.65 (m, 5H), 3.57 (t, J=5.2 Hz, 2H), 3.34-3.39 (m, 6H), 2.87 (t, J=6.5 Hz, 2H), 2.76 (t J=6.2 Hz, 2H), 1.96-2.00 (m, 4H), 1.44 (s, 9H).

Compound 3B $^1$H NMR (500 MHz, CDCl$_3$): a (ppm)= 8.60 (s, 1H), 8.56 (s, 1H), 7.00 (s, 1H), 6.22 (br, 1H), 4.53 (br, 1H), 3.35-3.40 (m, 6H), 3.11 (m, 2H), 2.87 (t, J=6.2 Hz, 2H), 2.76 (t, J=6.1 Hz, 2H), 1.96-2.00 (m, 4H), 1.44 (s, 9H), 1.44-1.50 (m, 4H), 1.35-1.38 (m, 4H).

Compound 3C $^1$H NMR (500 MHz, CDCl$_3$): a (ppm)= 8.60 (s, 1H), 8.53 (s, 1H), 6.99 (s, 1H), 6.97 (br, 1H), 5.01 (br, 1H), 3.72 (m, 2H), 3.63-3.67 (m, 6H), 3.59 (m, 2H), 3.52-3.56 (m, 4H), 3.35-3.39 (m, 4H), 3.22 (m, 2H), 2.87 (t, J=6.4 Hz, 2H), 2.76 (t, J=6.2 Hz, 2H), 1.96-2.00 (m, 4H), 1.88 (m, 2H), 1.75 (m, 2H), 1.43 (s, 9H).

GogiFreSH

3A-C →(1. TFA; 2. indomethacin/ EDCl/HOBt/DIEA)

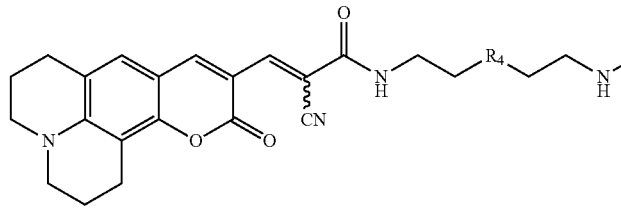
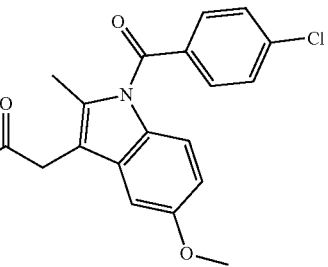

GolgiFreSH-A/B/C

-R₄- = -OCH₂CH₂O-     A
    = -CH₂CH₂-         B
    = -CH₂(OCH₂CH₂)₂OCH₂-  C

Compound 3 was dissolved in a solution of trifluoroacetic acid (TFA)/dichloromethane (1/1), and then stirred at room temperature for 1 to 2 hours. The solvent was removed by distillation under reduced pressure, and the remaining compound, indomethacin (1.1 eq.), HOBt (2.5 eq.), DIEA (3.0 eq.) and EDCI (2.5 eq.) were dissolved in DMF, and the solution was stirred at room temperature for 7 to 8 hours. The solvent was removed by distillation under reduced pressure, and the remaining mixture was diluted with EtOAc, and then washed with a saturated aqueous solution of NaCl. The organic layer was separated, dried with Na₂SO₄, and then to filtered, and the filtrate was distilled under reduced pressure to remove the solvent. The remaining mixture was purified by SiO₂ column chromatography to obtain GolgiFreSH GolgiFreSH-A (formula VII) ¹H NMR (500 MHz, CDCl₃): a (ppm)=8.52 (s, 1H), 8.49 (s, 1H), 7.64 (d, J=8.6 Hz, 2H), 7 46 (d, J=86 Hz, 2H), 6.93 (d, J=2.3 Hz, 1H), 6.89 (s, 1H), 6.80 (d, J=9.1 Hz, 1H), 6.61-6.63 (m, 2H), 6.39 (t, J=5.6 Hz, 1H), 3.80 (s, 3H), 3.65 (s, 2H), 3.48-3.55 (m, 10H), 3.44 (m, 2H), 3.35-3.39 (m, 4H), 2.86 (t, J=62 Hz, 2H), 2.72 (t, J=6.5 Hz, 2H), 2.40 (s, 3H), 1.95-1.99 (m, 4H).

GolgiFreSH-B (formula VIII) ¹H NMR (500 MHz, CDCl₃): a (ppm)=8.57 (s, 1H), 8.50 (s, 1H), 7.66 (m, 2H), 7.48 (m, 2H), 6.98 (s, 1H), 6.90 (d, J=2.4 Hz, 1H), 6.87 (d, J=9.1 Hz, 1H), 6.69 (dd, 3J=9.1 Hz, 4J=2.4 Hz, 1H), 6.23 (t, J=5.7 Hz, 1H), 5.78 (t, J=5.8 Hz, 1H), 3.82 (s, 3H), 3.65 (s, 2H), 3.28-3.39 (m, 6H), 3.20 (m, 2H), 2.86 (t J=6.4 Hz, 2H), 2.76 (t, J=6.2 Hz, 2H), 2.39 (s, 3H), 1.95-2.00 (m, 4H), 1.50 (m, 2H), 1.42 (m, 2H), 1.22-1.31 (m, 4H); HRMS (m/z): [M+Na]+ 7692772.

GolgiFreSH-C (formula IX) ¹H NMR (500 MHz, CDCl₃): a (ppm)=8.55 (s, 1H), 8.48 (s, 1H), 7.67 (d, J=8.0 Hz, 2H), 7.47 (d, J=8.0 Hz, 2H), 6.98 (L J=4.9 Hz, 1H), 6.96 (s, 1H), 6.92 (s, 1H), 6.87 (d, J=9.0 Hz, 1H), 6.66 (d, J=9.0 Hz, 1H), 6.34 (t J=4.9 Hz, 1H), 3.81 (s, 3H), 3.57-3.63 (m, 8H), 3.42-3.51 (m, 8H), 3.31-3.38 (m, 6H), 2.85 (t, J=62 Hz, 2H), 2.75 (t, J=5.9 Hz, 2H), 2.37 (s, 3H), 1.95-1.99 (m, 4H), 1.84 (m, 2H), 1.71 (m, 2H); HRMS (m/z): [M+Na]+ 900.3390.

Example 1: Experimental Materials and Methods 1-1. Reagents

Diamide and Antimycin A were purchased from Sigma-Aldrich. BODIPY TR C5-ceramide was purchased from Thermo Fisher Scientific.

1-2, In Vitro Reaction of FreSH-Tracer (Fluorescent Real-Time SH Group-Tracer) Compound with Thiol Compound A buffer (10 mM phosphate, 150 mM NaCl, pH 7.4, H₂O:DMSO=98:2) containing a mixture of a glutathione compound (0-100 mM) and a FreSH-tracer compound V (10 μM) was prepared, and the time-dependent UV-Vis absorption spectrum and fluorescence emission spectrum of the buffer were measured with SCINCO S-3100 spectrophotometer and Hitachi F-7000 spectrophotometer (see FIG. 2), respectively.

1-3. Measurement of Kd Value of Thiol Compound

After a chemical equilibrium between the glutathione compound (0-100 mM) and the FreSH-tracer-derived compound was formed by an in vitro reaction, the emission spectrum of fluorescence emitted upon excitation with light at a wavelength of 430 nm was measured. The relationship between the fluorescence intensity at the maximum emission wavelength (580 nm) and the concentration of the thiol compound was analyzed by non-linear regression, thereby determining the chemical equilibrium constant (Kd, 1-5 mM) between the thiol compound and the FreSH-tracer.

1-4. Cytotoxicity Assay (MTT Assay)

HeLa cells (5×10³ cells/well) were cultured in a 96-well dish for 18 hours, and then treated with dimethyl sulfoxide (DMSO), MitoFreSH-tracer (formulas III to V) or Golgi-FreSH-tracer (formulas VII to IX) for 24 hours. After washing with PBS, the cells were incubated in methylthiazolyldiphenyl-tetrazolium bromide (MTT) solution (500 μg/mL medium) for 3 to 4 hours. After removal of the MTT solution, the formazan crystal was dissolved in DMSO, and then the absorbance at 570 nm was measured. LD50 (50% Lethal Dose) was calculated using Graphpad 5.0 software (see FIG. 3).

1-5. Real-Time Imaging of Living Cells

HeLa cells were cultured in DMEM (containing 10% heat-inactivated FBS (Hyclone), 100 U/ml of penicillin, 100 μg/ml of streptomycin sulfate and 2 mM glutamine aid free of phenol red). HeLa cells were seeded in 35 mm cover glass bottom dishes (SPL Life Sciences), and then cultured under the conditions of 37° C. and 5% CO₂ for foe indicated time. Before observation using a fluorescence microscope, the HeLa cells were incubated with 2 mL of a medium containing 10 μM of the FreSH-tracer-derived compound for 0.5 to 1.5 hours. After washing twice with PBS, real-time images of the cells were acquired using a Nikon A1 laser scanning confocal microscope. The imaging test was performed while the cells were incubated under foe conditions of 37° C. and 5% $CO_2$ in a chamber mounted in a Nikon ECLIPSE Ti inverted microscope equipped with CFI Plan apochromat 60× and 1.40 numerical aperture (NA) objective lenses. The FreSH-tracer-derived compound was excited with laser beams at 403 nm and 488 nm, and the fluorescence of the tracer-derived compound was detected through filters with 500-550 nm and 570-620 nm band intervals, respectively. Using NIS-Elements AR software, the experimental data were analyzed and the ratio of fluorescence was imaged (see FIGS. 4 and 5).

1-6. High-Throughput Cell Imaging

HeLa cells were cultured in DMEM (containing 10% heat-inactivated FBS (Hyclone), 100 U/ml of penicillin, 100 μg/ml of streptomycin sulfite and 2 mM glutamine and free of phenol red). HeLa cells were seeded in Greiner 96-well dishes (Sigma-Aldrich), and then cultured under the conditions of 37° C. and 5% $CO_2$ for the indicated time. Before observation using a fluorescence microscope, the HeLa cells were incubated with a medium containing 10 μM of the GolgiFreSH-tracer for 0.5 to 1.5 hours. After washing twice with Hank's balanced salt solution, real-time images of the cells were acquired using an Operetta High-Content Imaging System (PerkinElmer). The imaging test was performed while the cells w ere incubated under the conditions of 37° C. and 5% $CO_2$ in a chamber mounted in the microscope. The GolgiFreSH-tracer was excited with LED light at 410-430 nm and 490-510 nm, and the fluorescence of the tracer was detected through filters with 460-540 nm and 560-630 nm band intervals, respectively. BODIPY TR C5ceramide was excited with LED light at 560-580 nm, and the fluorescence thereof was detected through filters with 590-640 nm band intervals. Using the Harmony software, the experimental data were analyzed (see FIGS. 4, 5 and 8).

Example 2: Measurement of Antioxidant Activity of Cell Organelle Mitochondria 2-1. Observation of the Property of MitoFreSH-Tracer that Reacts Ratiometrically, Reversibly and Rapidly with GSH When glutathione was added to the MitoFreSH-tracer while the concentration of glutathione increased, the absorbance of the tracer for UV light and visible light increased at Emax=430 nm and decreased at Emax=520 nm (FIG. 2B), and the fluorescence emission intensity of the tracer increased at about 510 nm (F510, Eex=430 nm; Eem=510 nm) and decreased at about 580 nm (F 580, Eex=520 nm, Eem=580 nm) (Kd=1.3 mM, FIGS. 2B and 2C). The present inventors have found that the ratio of the fluorescence emission intensity of F510 to the fluorescence emission intensity of F580 (F510/F580) of the MitoFreSH-tracer charges in proportion to a wide range of the GSH concentration (FIG. 2D). This suggests that the tracer can be used as a radiometric sensor. The regression curve obtained from the fluorescence intensity ratio indicated linearity ($R^2$=0.9836) in a concentration range (0-20 mM) wider than the concentration of glutathione present in the cells (insert in FIG. 2D).

The above data suggest that the MitoFreSH-tracer has the most suitable sensor property for monitoring the intracellular glutathione level.

2-2. Visualization of Changes in Mitochondrial Glutathione Levels in Living Cells by Ratiometric Analysis of MitoFreSH-Tracer The present inventors have studied the applicability of the MitoFreSH-tracer to examination of changes in mitochondrial glutathione levels in living cells. The present inventors could describe typical mitochondrial staining patterns as false color images based on the fluorescence intensity ratio measured by confocal microscope measurement during culture of HeLa cells in medium supplemented with 10 μM nontoxic MitoFreSH-tracer for at least 24 hours (FIG. 4A). In the present invention, in order to examine whether the sensor responds to the oxidation/reduction conditions of mitochondrial glutathione, living cells loaded with the sensor were treated with 0.5 mM diamide (DA) to oxidize intracellular glutathione. It was found that, when diamide was added to the culture medium, an immediate sensor reaction in the living cells was induced (FIGS. 4B and 4C). The sensor fluorescence intensity ratio calculated from images of the living cells was reduced by treatment with diamide (FIGS. 4B and 4C).

Next, the present inventors examined changes in the fluorescence of the MitoFreSH-tracer examined changes in the fluorescence of the MitoFreSH-tracer under the conditions where reactive oxygen species are generated in mitochondria. It was confirmed that when cells were treated for 75 minutes with antimycin A that increases the generation of reactive oxygen species by interfering with the election transport chain in mitochondria, the fluorescence intensity ratio of the MitoFreSH-tracer decreased depending on the concentration of antimycin A (FIGS. 5A and 5B).

Therefore, based on the above experimental results, the present inventors demonstrated that the MitoFreSH-tracer can be used to monitor charges in the level of GSH in the mitochondria of living cells in teal time.

Example 3: Measurement of Antioxidant Activity of Cell Organelle Golgi Apparatus 3-1. Analysis of Glutathione Level in Living Cells by Radiometric Analysts of GolgiFreSH-Tracer The present inventors investigated whether the Golgi-FreSH-tracer would be maintained in cells and applicable to the investigation of changes in the level of glutathione in the Golgi apparatus of living cells. After addition of the Golgi-FreSH-tracer tracer to the cell culture medium, changes in the fluorescence intensity in the cells and the ratio of fluorescence intensity in the cell were observed. The position of the fluorescence measured by high-throughput cell imaging in HeLa cells loaded with the GolgiFreSH-tracer and the Golgi apparatus marker BODIPY TR C5-ceramide was examined, and as a result, it was could be observed that the F510 of the GolgiFreSH-tracer mostly overlapped with the fluorescence of BODIPY TR C5-ceramide, indicating that the GolgiFreSH-tracer was located in the Golgi apparatus (FIG. 7). In order to examine whether the sensor responds to the oxidation/reduction conditions of intracellular glutathione, the present inventors oxidized intracellular glutathione by sensor-loaded living cells with 1 mM diamide. It was observed that when diamide was added to the culture medium, a sensor reaction in the living cells was induced (FIG. 8A). The sensor fluorescence intensity ratio calculated from images of tire living cells was reduced by treatment with diamide (FIG. 8B). Next, living cells were treated with various concentrations of diamide and analyzed, and as a result, it could be seen that the fluorescence intensity ratio of the GolgiFreSH-tracer decreased depending on the concentration of diamide (FIG. 9). Therefore, based on tire above experimental results, the present inventors demonstrated that the GolgiFreSH-tracer can be used to monitor changes in the level of glutathione in the Golgi apparatus of living cells in real time.

The use of the compound or composition according to the present invention can measure the antioxidant activity of the organelle mitochondria or Golgi apparatus in living cells. When this compound or composition is applied to stem cells, highly active stem cells can be screened based on the results of measuring antioxidant activity in stem cells, thereby increasing the efficiency of cell therapeutic agents.

All the references, articles, publications, patents and patent applications cited in this specification are incorporated herein in their entirety. Therefore, the spirit and scope of the appended claims should not be limited to the description of the preferred embodiments contained herein.

INDUSTRIAL APPLICABILITY

When the composition comprising the compound according to the present invention is used, it can measure the antioxidant activity of the organelle mitochondria or Golgi apparatus in living cells, particularly stem cells, and am screen highly active stem cells based on the results of measuring the antioxidant activity of the cell organelle.

The invention claimed is:
1. A compound having Formula V or Formula VI or a pharmaceutically acceptable salt thereof

[Formula V]

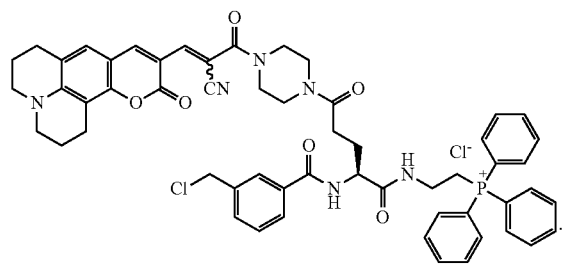

[Formula VI]

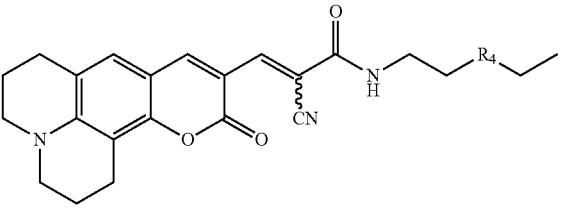

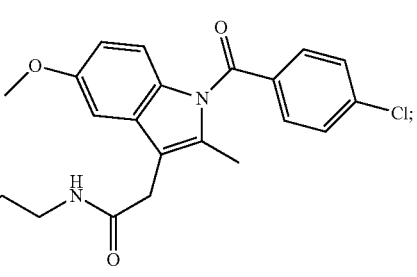

wherein $R_4$ is $(CH_2)p\text{-}(OCH_2CH_2O)q\text{-}(CH_2)r$, or $-(CH_2CH)s\text{-}$, wherein p and r are each independently integer ranging from 0 to 5, and q and s are each independently integer ranging from 1 to 5.

2. The compound or pharmaceutically acceptable salt according to claim 1, having Formula VII, Formula VIII, or Formula IX:

[Formula VII]

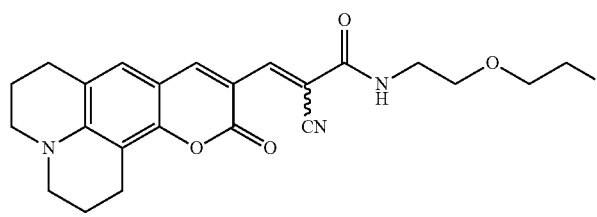

[Formula VIII]

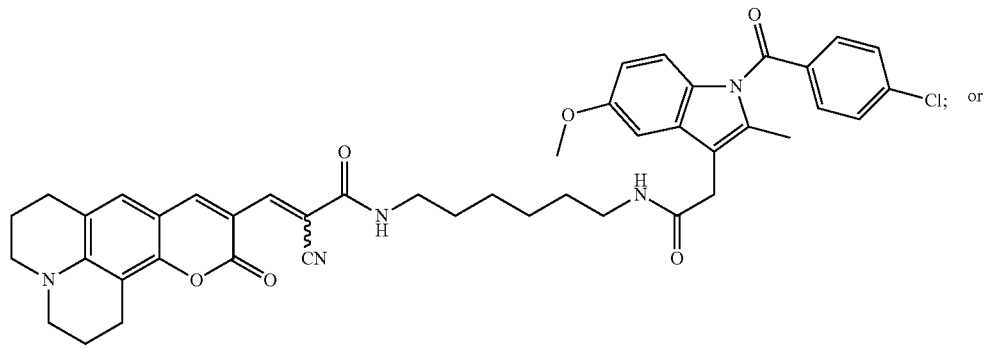

or

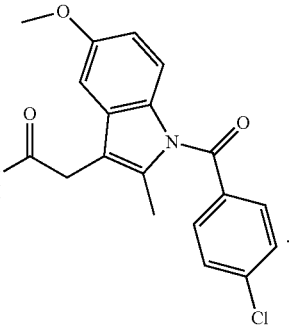

[Formula IX]

3. The compound or pharmaceutically acceptable salt according to claim 1, wherein the compound exhibits a maximum emission wavelength at 550-680 nm in a free state, and exhibits a maximum emission wavelength at 430-550 nm in a thiol-bound state.

4. A method for measurement of antioxidant activity in living cells, the method comprising combining with the living cells a compound or pharmaceutically acceptable salt according to claim 1.

5. The method of claim 4, wherein the measurement of the antioxidant activity is measurement of the level of thiols in the living cells.

6. The method of claim 5, wherein the measurement of the level of thiols is measurement of the level of thiols in cell organelles.

7. The method of claim 6, wherein the cell organelles are mitochondria or Golgi apparatus.

8. The method of claim 7, wherein the compound or pharmaceutically acceptable salt has Formula VII, Formula VIII, or Formula IX:

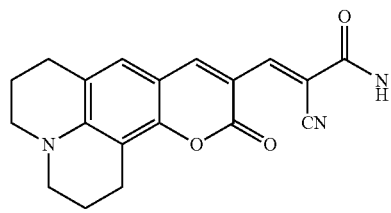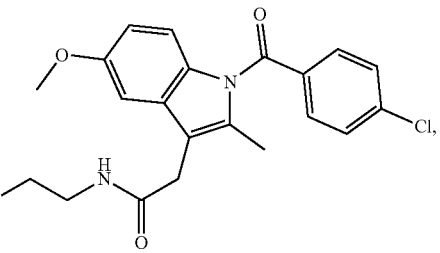

[Formula VII]

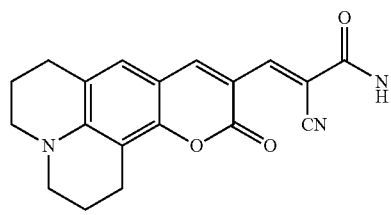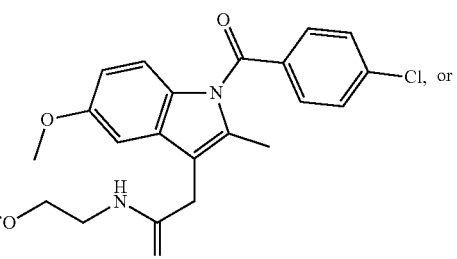

[Formula VIII]

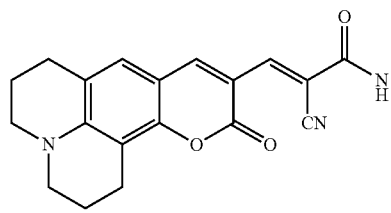
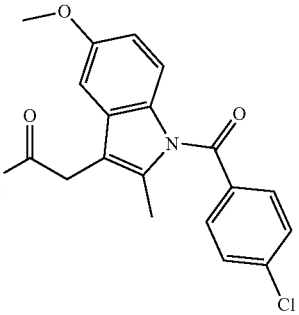

[Formula IX]

or is a pharmaceutically acceptable salt thereof.

9. The method of claim 6,
wherein, as the level of thiols in the measurement of the level of thiols increases, the fluorescence intensity at 550-680 nm decreases and the fluorescence intensity at 430-550 nm increases,
wherein the measurement of the level of thiols is performed by obtaining the ratio of the fluorescence intensity at 430-550 nm to the fluorescence intensity at 550-680 nm,
wherein the ratio is a relationship between the fluorescence intensity at 430-550 nm and the fluorescence intensity at 550-680 nm.

10. The method of claim 6, wherein the measurement of the level of thiols indicates a degree of oxidative stress of the cells; a degree of oxidation of the cells; or a degree of aging of the cells.

11. A kit for diagnosing an oxidative stress-induced disease, comprising a compound or pharmaceutically acceptable salt according to claim 1.

12. The compound or pharmaceutically acceptable salt according to claim 1, having Formula V:

[Formula V]

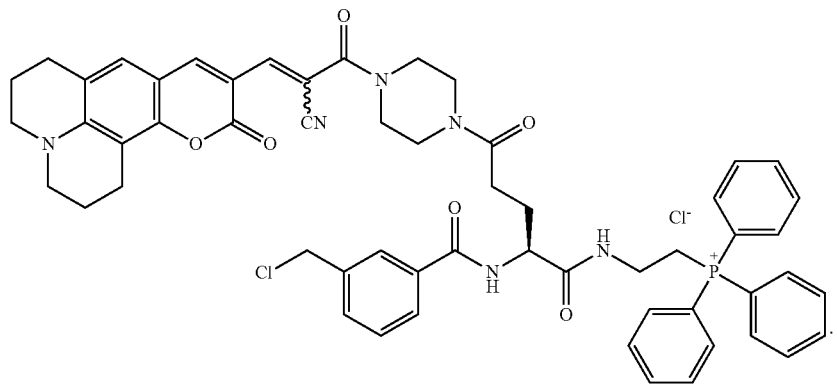

13. The compound or pharmaceutically acceptable salt according to claim 1, having Formula VI:

[Formula VI]

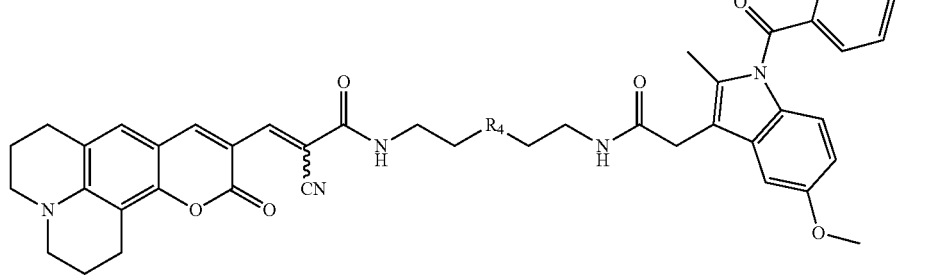

wherein $R_4$ is $(CH_2)p\text{-}(OCH_2CH_2O)q\text{-}(CH_2)r$, or $-(CH_2CH_2)s\text{-}$,
wherein p and r are each independently integer ranging from 0 to 5, and q and s are each independently integer ranging from 1 to 5, or a pharmaceutical salt thereof.

14. A method for measurement of antioxidant activity in living cells, the method comprising combining with the living cells a compound or pharmaceutically acceptable salt according to claim 12.

15. A method for measurement of antioxidant activity in living cells, the method comprising combining with the living cells a compound or pharmaceutically acceptable salt according to claim 13.

* * * * *